（12）United States Patent
Swanson et al.

(10) Patent No.: US 10,842,412 B2
(45) Date of Patent: Nov. 24, 2020

(54) SYSTEMS AND METHODS TO ESTIMATE HUMAN LENGTH

(71) Applicant: PIXA4 LLC, Seattle, WA (US)

(72) Inventors: James Martin Swanson, Seattle, WA (US); Robert Clay Isenhart, Brooklyn, NY (US)

(73) Assignee: PIXA4 LLC, Seattle, WA (US)

( * ) Notice: Subject to any disclaimer, the term of this patent is extended or adjusted under 35 U.S.C. 154(b) by 191 days.

(21) Appl. No.: 16/174,940

(22) Filed: Oct. 30, 2018

(65) Prior Publication Data

US 2019/0125215 A1 May 2, 2019

Related U.S. Application Data

(60) Provisional application No. 62/579,414, filed on Oct. 31, 2017.

(51) Int. Cl.
*A61B 5/107* (2006.01)
*A61B 5/00* (2006.01)
(Continued)

(52) U.S. Cl.
CPC .......... *A61B 5/1072* (2013.01); *A61B 5/1079* (2013.01); *A61B 5/4561* (2013.01);
(Continued)

(58) Field of Classification Search
CPC ........ A61B 5/1072; A61B 5/1079; G06T 7/60
(Continued)

(56) References Cited

U.S. PATENT DOCUMENTS 4,885,844 A * 12/1989 Chun .................. A41H 1/02
33/15
6,468,233 B2 * 10/2002 Cook .................. A61B 5/103
33/514.2
(Continued)

FOREIGN PATENT DOCUMENTS

CN 103156613 A 6/2013
CN 106525212 A 3/2017
(Continued)

OTHER PUBLICATIONS

Shrestha, et al., "Computational Imaging with Multi-Camera Time-of-Flight Systems," ACM SIGGRAPH (Transactions on Graphics 34, 5), 2016, 11 pages.
(Continued)

*Primary Examiner* — George B Bennett
(74) *Attorney, Agent, or Firm* — Knobbe, Martens, Olson & Bear, LLP

(57) ABSTRACT

Systems and methods use a three-dimensional snapshot of an infant, child, adolescent, or adult where the subject may have bent legs and an unaligned head position, to provide an estimate of human length. The system identifies anatomical features from the digital information and generates a virtual skeleton. The cumulative distances between pseudo-joints of the virtual skeleton provide an estimate of human length. Comparing length estimates from multiple three-dimensional snapshots of the same individual acquired over time provide an indication of growth of the infant, child, or adolescent. Daily estimates of length can detect growth faltering sooner than less frequent estimates of length, which can lead to timely intervention.

20 Claims, 18 Drawing Sheets

(51) Int. Cl.
*G06T 7/62* (2017.01)
*G01G 19/50* (2006.01)

(52) U.S. Cl.
CPC .............. *G06T 7/62* (2017.01); *A61B 5/0077* (2013.01); *A61B 5/706* (2013.01); *G01G 19/50* (2013.01); *G06T 2207/10028* (2013.01); *G06T 2207/20044* (2013.01); *G06T 2207/30196* (2013.01)

(58) Field of Classification Search
USPC .................................................. 33/511, 512
See application file for complete search history.

(56) References Cited

U.S. PATENT DOCUMENTS

| | | | |
|---|---|---|---|
| 8,565,479 | B2 | 10/2013 | Gurman et al. |
| 2005/0154487 | A1* | 7/2005 | Wang ........................ A41H 1/00 700/132 |
| 2013/0305547 | A1* | 11/2013 | Grove ....................... A41H 3/00 33/17 A |
| 2014/0360030 | A1* | 12/2014 | Grove ....................... A41H 3/04 33/17 R |
| 2015/0026990 | A1* | 1/2015 | Ellis ......................... A41H 3/04 33/15 |
| 2015/0223730 | A1 | 8/2015 | Ferrantelli |
| 2017/0209075 | A1 | 7/2017 | Lewandowski |
| 2017/0273639 | A1 | 9/2017 | Iscoe et al. |

FOREIGN PATENT DOCUMENTS

| | | |
|---|---|---|
| CN | 106725497 A | 5/2017 |
| EP | 2 095 296 A1 | 9/2009 |
| KR | 101338324 B1 | 12/2013 |
| WO | WO 2015/116563 A1 | 8/2015 |
| WO | WO 2008/128568 A1 | 10/2015 |
| WO | WO 2017/085087 A1 | 5/2017 |
| WO | WO 2017/099580 A1 | 6/2017 |

OTHER PUBLICATIONS

Lampl, "Perspectives on modelling human growth: Mathematical models and growth biology," Ann Hum . Biol Downloaded from informahealthcare.com by 69.127.56.230 on Jul. 28, 2012.
Lampl, "Saltation and Stasis: A Model of Human Growth," Science, vol. 258, Oct. 30, 1992, pp. 801-803.
"PhotoModeler," 2013 Eos Systems Inc., 3 pages.
"Analysis: Single Image Photogrammetry," HOSDB Sep. 2007, 38 pages.
Papageorghiou, et al., "Ultrasound methodology used to construct the fetal growth standards in the Intergrowth-21st Project," 2013 Royal College of Obstetricians and Gynaecologists, pp. 27-32.
The Baby Box Co., https://checkout.shopify.com/2627775/checkouts/f4316c4aa00d66509bba461a39c8fa01/thank you, 2 pages.
Foderaro, "Baby in a Box? Free Cardboard Bassinets Encourage Safe Sleeping," Baby in a Box? Free Cardboard Bassinets Encourage Safe Sleeping—The New York Times, 2017, 5 pages.
Sokolover, et al., "A novel technique for infant length measurement based on stereoscopic vision," Arch Dis Child 2014;99:625-628. doi:10.1136/archdischild-2013-304291.
Swanson, et al., "Young adult outcomes in the follow-up of the multimodal treatment study of attention-deficit/hyperactivity disorder: symptom persistence, source discrepancy, and height suppression," Journal of Child Psychology and Psychiatry, 2017, 16 pages.
Swanson, et al.,"Effects of Stimulant Medication on Growth Rates Across 3 Years in the MTA Follow-up," J. Am. Acad. Child Adolesc. Psychiatry, 46:8, Aug. 2007, 13 pages.
MTA Cooperative Group, "National Institute of Mental Health Multimodal Treatment Study of ADHD Follow-up: Changes in Effectiveness and Growth After the End of Treatment," Pediatrics vol. 113 No. 4 Apr. 2004, 8 pages.
International Search Report and Written Opinion dated Feb. 5, 2019 for International Application No. PCT/US2018/058281, 16 pages.

* cited by examiner

SYSTEMS AND METHODS TO ESTIMATE HUMAN LENGTH

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Indications of growth in infants, children, and adolescents are used to evaluate physical development and are important gauges of overall health. Length is a key indicator of growth. For measuring length of an infant, an infantometer is used by trained personnel to measure the crown-to-heel length. Use of the infantometer involves placing the infant on its back on a plate, straightening the legs such that the infant's foot rests on a foot plate, aligning the head to rest on a head plate, and measuring the length of the infant with a ruler attached to the infantometer. This process causes distress in the infant. Reluctance by medical personnel to completely stretch the infant could lead to inaccurate measurements, and variation within and across personnel could lead to unreliable measurements. For measuring children, adolescents, and adults, a stadiometer is used. Use of the stadiometer involves having the child, adolescent, or adult stand on a plate or the floor, with the back to a perpendicular wall or rod, assuming an upright stance, and looking forward with the head in the Frankfurt plane. The process to ensure upright posture and the correct head position requires trained personnel to measure crown-to-heel length, and variation within and across personnel could lead to unreliable measurements.

SUMMARY

A reliable measure of the growth as the change in length of a developing infant, child, or adolescent can be estimated from computer processing of data from optical sensors that provide information sufficient to create three-dimensional images. One way to accomplish this is with sophisticated algorithms to transform these images into repeatable estimates of a pseudo skeleton. This not an instance of bone structure but a framework that connects a set of simulations of joints such as ankles, knees, hips and neck that are located in three dimensional space hereafter referred to as 3D. These features, hereafter referred to as anatomical landmarks, may be combined such that a summation of distances along the length of the resulting stick figure may provide an accurate estimate of length of an infant, child, adolescent, or adult. Another way to accomplish this is by aligning the head position and straightening the legs so a point or location on the head and a point or location on the legs are on a straight line that provides an accurate estimate of length on a subject, where the subject can be, for example, an infant, child, adolescent or adult.

Systems and methods are disclosed to provide an indication of growth by measuring changes in length between anatomical landmarks located by one or more computational algorithms on a 3D image. These partial length estimates are summed to form an overall length estimate that is independent of small postural variation.

Further, system and methods are disclosed to acquire a three-dimensional image of a subject in a natural supine or upright position from a snapshot, such as a digital snapshot can be taken of the frontal surface of the subject using a time-of-flight camera. In an embodiment, the acquired 3D image is noisy as there are limitations to the accuracy and resolution of any measurement. However a computational algorithm that emphasizes detection and use of large anatomical features that are points of inflection where the body naturally bends can be used to minimize the noise. The systems and methods can use digital filtering and point-cloud processing to identify anatomical features of an infant, child, adolescent, or adult from the acquired 3D image. A point-cloud is a set of points in 3D space. Point-cloud processing can be characterized as computational manipulation of the point-cloud of an object to generate a 3D surface representing the object. The identified anatomical features can be used to provide estimations of total crown-to-heel length or partial length between natural landmarks on the body, where partial length is the distance between at least two natural landmarks and is less than the total length. Comparisons over a period of time of the estimated lengths can provide an indication of growth, which depends on the stage of development when an individual is growing (i.e., in infancy, childhood, or adolescence). The measures of length can provide an indication of whether the infant, child, or adolescent is developing or growing normally. Advantageously, point-cloud processing can identify the anatomical features for accurate and reliable estimation of the length from the noisy 3D images, despite bent legs, unaligned head positions, and different postures in images acquired at different times.

Aspects of the disclosure relate to a computer-implemented method to estimate length of a subject from a three-dimensional image. The computer-implemented method comprises acquiring a three-dimensional image of a subject; processing the three-dimensional image of the subject to generate a digital representation of the subject; and processing the digital representation of the subject to determine at least a partial length of the subject, wherein the subject is an infant, child, adolescent, or adult.

In an embodiment, processing the digital representation of the subject to determine at least the partial length of the subject comprises processing the digital representation of the subject to generate a virtual skeleton of the subject; and measuring distance along at least a portion of the virtual skeleton to provide an estimate of at least partial length of the subject.

In an embodiment, processing the digital representation of the subject to generate the virtual skeleton of the subject comprises locating a plurality of peaks and troughs in a point cloud representation of the subject; locating a natural landmark associated with human anatomy in each of ones of at least a portion of the plurality of peaks and troughs; fitting spheres to model the located natural landmarks; and locating centers of spheres to form the virtual skeleton.

In an embodiment, measuring distance along at least the portion of the virtual skeleton comprises measuring distance between at least two sphere centers along the virtual skeleton to provide the estimate of at least partial length of the subject. In another embodiment, locating the plurality of peaks and troughs comprises determining derivatives in length and width planes of the point cloud representation of the subject. In a further embodiment, fitting the spheres comprises detecting a set of extrema on surface of the point cloud representation of the subject and sizing the spheres based on the detected set of extrema.

In an embodiment, the digital representation of the subject comprises a point cloud representation of the subject. In another embodiment, the three-dimensional image is acquired by a time of flight device. In a further embodiment, the three-dimensional image is generated from a plurality of two-dimensional images.

In an embodiment, the three-dimensional image of the subject comprises a three-dimensional image of the subject on a mat that has defined edges and the digital representation of the subject comprises a digital representation of the subject without the mat.

Aspects of the disclosure relate to a system to estimate length of a subject from a three-dimensional image. The system comprises one or more computing devices associated with a measurement system, where the subject measurement system is configured to acquire a three-dimensional image of a subject; process the three-dimensional image of the subject to generate a digital representation of the subject; and process the digital representation of the subject to determine at least a partial length of the subject, wherein the subject is an infant, child, adolescent, or adult.

Aspects of the disclosure relate to a computer-implemented method to estimate length of a subject from a three-dimensional image, the computer-implemented method comprising acquiring, from a time-of-flight device, a three-dimensional image of a subject on a mat that has defined edges; processing the three-dimensional image to generate a point cloud representation of the subject without the mat; locating a plurality of peaks and troughs in the point cloud representation of the subject; locating a natural landmark associated with human anatomy in each of ones of at least a portion of the plurality of peaks and troughs; fitting spheres to model the located natural landmarks; locating centers of spheres to form a virtual skeleton; and measuring distance between at least two sphere centers along the virtual skeleton to provide an estimate of at least partial subject length.

In an embodiment, the mat has known dimensions. In another embodiment, the defined edges comprise one or more defined corners. In a further embodiment, the time-of-flight device comprises a time-of-flight camera.

In an embodiment, the three-dimensional image includes a depth image and an amplitude image of brightness. In another embodiment, the three-dimensional digital image includes an amplitude value associated with the brightness information and a distance value associated with the depth information. In a further embodiment, processing the three-dimensional image to generate a point cloud representation of the subject without the mat comprises smoothing the depth image with one or more spatial filters to generate one or more secondary images; rotating a view perspective of each of the one or more secondary images to align a plane of the time-of-flight device with the plane of the mat; removing points on the one or more rotated secondary images with values less than an estimated noise threshold to remove the mat; and combining the one or more mat-removed secondary images to form the point cloud representation of the subject.

In an embodiment, locating the peaks and troughs comprises determining derivatives in the length and width planes of the point cloud representation to located peaks and troughs. In another embodiment, fitting the spheres comprises detecting a set of extrema on surface of point cloud representation of the subject and sizing the spheres based on the detected set of extrema.

In an embodiment, the computer-implemented method further comprises determining an indication of growth by comparing a first estimate of growth from a first three-dimensional image taken at a first earlier time with a second estimate of growth from a second three-dimensional image taken at a second later point in time.

Aspects of the disclosure relate to a system to estimate length of a subject from a three-dimensional image. The system comprises one or more computing devices associated with a measurement system, wherein the measurement system is configured to acquire, from a time-of-flight device, a three-dimensional image of a subject on a mat that has defined edges; process the three-dimensional image to generate a point cloud representation of the subject without the mat; locate a plurality of peaks and troughs in the point cloud representation of the subject; locate a natural landmark associated with human anatomy in each of ones of at least a portion of the plurality of peaks and troughs; fit spheres to model the located natural landmarks; locate centers of spheres to form a virtual skeleton; and measure distance between at least two sphere centers along the virtual skeleton to provide an estimate of at least partial length.

In an embodiment, processing the three-dimensional image to generate a point cloud representation of the subject without the mat comprises smoothing the depth image with one or more spatial filters to generate one or more secondary images. In another embodiment, processing the three-dimensional image to generate a point cloud representation of the subject without the mat further comprises rotating a view perspective of each of the one or more secondary images to align a plane of the time-of-flight device with the plane of the mat. In a further embodiment, processing the three-dimensional image to generate a point cloud representation of the subject without the mat further comprises removing points on the one or more rotated secondary images with values less than an estimated noise threshold to remove the mat. In a yet further embodiment, processing the three-dimensional image to generate a point cloud representation of the subject without the mat further comprises combining the one or more mat-removed secondary images to form the point cloud representation of the subject.

In an embodiment, locating the peaks and troughs comprises determining derivatives in the length and width planes of the point cloud representation to located peaks and troughs. In another embodiment, fitting the spheres comprises detecting a set of extrema on surface of point cloud representation of the subject and sizing the spheres based on the detected set of extrema. In a further embodiment, the measurement system is further configured to determine an indication of growth by comparing a first estimate of growth from a first three-dimensional image taken at a first earlier time with a second estimate of growth from a second three-dimensional image taken at a second later point in time.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

Throughout the drawings, reference numbers are re-used to indicate correspondence between referenced elements. The drawings, associated descriptions, and specific implementation are provided to illustrate embodiments for measuring the length of an infant, but does not to limit the scope of the disclosure to other stages of development (i.e., to measures of a child, adolescent, or adult). A subject can be an infant, child, adolescent, or adult.

DETAILED DESCRIPTION

Figure 1A:
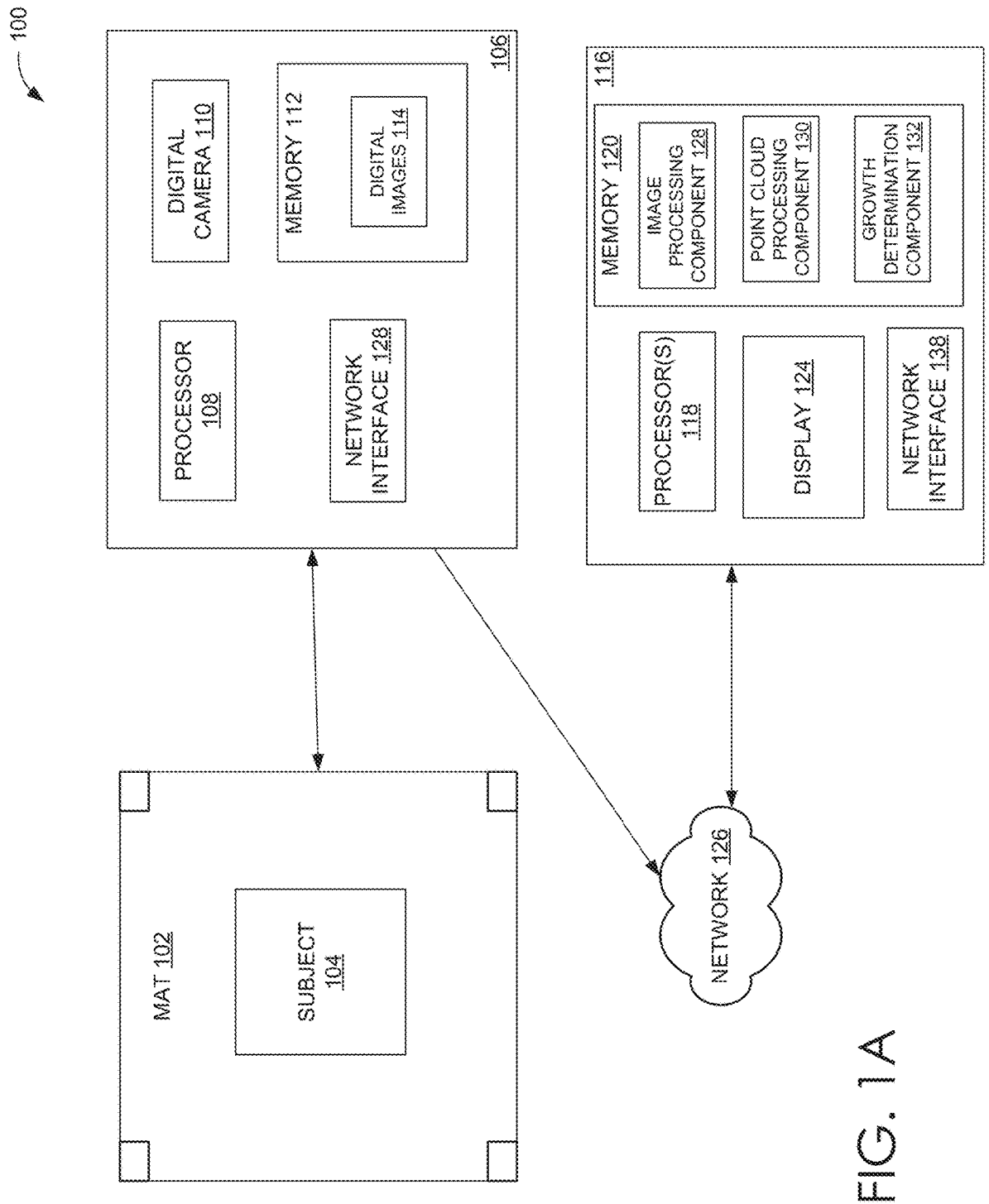
FIG. 1A illustrates a block diagram of an example system to acquire and process 3D digital images of a subject to provide an estimate of at least partial length of the subject using networked computer system, according to certain embodiments.

Auxology can be described as the science of human growth and development. Traditionally, human growth has been characterized as a continuous process because traditional auxology studies measure height and weight with relatively long periods of time between consecutive measurements, such as every few month for infants and biannually or annually for children and adolescents, for example. When the growth measurement data, such as the height and weight, are acquired a few times a year, each data point of the growth measurement data can be characterized as the summation of many individual growth periods. Summing many individual growth periods in each observation and using the distance between them as an increase in length may be misinterpreted as continuous growth between the observations.

Other human growth models propose that growth can be sporadic mini-growth spurts occurring approximately every 10-15 days, called saltations, each followed by a period of non-growth, called stasis. The characteristics of individual saltations and stasis periods are lost when growth is measured infrequently. To determine the frequency and amplitude of saltations, it is desirable to measure infant length daily. The frequency and amplitude of the saltations determined from daily measurements of infant length can be used to better understand the biology of human growth problems, such as deficits in amplitude of saltations, deficits in the frequency of saltations, and long periods of stasis. Further, daily measurements of infant length can detect growth faltering sooner than infrequent measurements, which can lead to timely intervention.

Traditional methods to measure infant length can be invasive, cumbersome, and expensive. For example, one method to measure the length of an infant is for trained technicians to place the infant on an infantometer, which is a device with a flat base and perpendicular headboard and footboard than can be adjusted to show the distance between them in millimeters. Typically, two technicians are required to obtain accurate and reliable measures of length.

The infantometer protocol is complex and difficult to follow. Typically the two technicians (a) place the infant on its back on the flat base, (b) align the infant's head to touch the headboard with the eyes in the "Frankfurt plane", (c) straighten the infant's legs horizontally and position the feet vertically, (d) adjust the footboard until it touches the infant's feet and heels, and (e) read and record the distance between the headboard and footboard. The Frankfurt plane is a plane passing through the inferior margin of the left orbit and the upper margin of each ear canal, which is parallel to the surface of the earth.

These procedures cause distress in the infant. Crying is common, and the infant is likely to struggle, creating difficulties for personnel engaged in positioning the infant. Accurate and reliable measurements are difficult to obtain. Due to these and other complications, obtaining frequent (e.g., daily) measures of length is onerous and is not often tried or accomplished.

The use of photos can offer an alternative that is not cumbersome and invasive. In an embodiment, a photograph can be taken with a device that can provide a 3D digital image from one or more photos (i.e., a snapshot(s)). For example, a device that includes a time-of-flight camera can provide the 3D digital image. Another example is use of a stereo camera and structured light. In an embodiment, the device can be a cell phone, a mobile device, a computer, a laptop, a tablet or the like that comprises a 3D imaging capability.

Most parents have a cell phone with a camera and parents enjoy taking snapshot photos of their children, especially in infancy. Embodiments disclosed herein do not require precise positioning of the infant, and do not because the distress associated with the infantometer procedures. Photos can be taken at standard times (upon awakening, at mealtime, after changing diapers, etc.) that can provide daily prompts for parents. The digital images from a 3D photo, or multiple 2D photos acquired from the parent's cell phone, for example, can be processed to provide lengths between the defined anatomical indicia generated from a photo or photos taken at a first time and compared to the lengths between the anatomical indicia generated from a photo of photos taken at a second time, such as the next day or the next week, for example. The multiple comparisons occurring over a period of time can provide an indication of the infant's growth.

There is a need to obtain a 3D image adequate to measure the length or a partial length of an infant (a) without specific equipment like an infantometer, (b) without trained personnel like the two-person team that uses an infantometer, (c) without touching the infant and causing distress while aligning the head and straightening and positioning the legs and feet, (d) without the variability associated with a person placing artificial landmarks on the infant each time an image is taken, and (e) without the use of multiple photos from different perspectives. A system and method that can be implemented easily in the home setting by parents to facilitate frequent and easy measurement of infant length is desirable.

FIG. 1A illustrates a block diagram of an example system 100 to acquire and process 3D digital images of a subject 104 to provide an estimate of at least partial length of the subject 104, according to certain embodiments. The subject 104 can be an infant, child, adolescent, or adult. The illustrated system 100 comprises a mat 102, a 3D image acquisition device 106, and an image processing and length estimation system 116. The 3D image acquisition device 106 and the image processing and length estimation system 116 communicate via a network 126. In some embodiments, the system 100 may include more or fewer components than those illustrated in FIG. 1A.

Network 126 may be any wired network, wireless network, or combination thereof. In addition, network 126 may be a personal area network, local area network, wide area network, cable network, fiber network, satellite network, cellular telephone network, data network, or combination thereof. In the example environment of FIG. 1A, network 126 is a global area network (GAN), such as the Internet. Protocols and components for communicating via the other aforementioned types of communication networks are well known to those skilled in the art of computer communications and thus, need not be described in more detail herein.

The mat 102 comprises a flat surface of known dimensions and with defined corners. For example, the mat can be constructed of soft foam, e.g. yoga mat, and the like. The flat mat can be produced in several sizes to accommodate a range of subject sizes. It is only required that the actual mat dimensions are known to the application software. It is also required that the entire mat is included in the photograph of the subject when the photograph is taken. In an embodiment, the corners of the mat 102 may be constructed with special marking, coloring, or other identification that makes the corners easy to recognize. The color of the remainder of the mat is chosen for low reflectivity of light at the frequency of illumination. It is required that the back of subject is in contact with the mat in certain anatomical regions. This permits the algorithm to compute a maximum depth measure for every point on the surface of the subject. The mat 102 is an example of a fixed background that the subject 104 may be placed on or against. In other embodiments, other backgrounds may be used.

The 3D image acquisition device may be implemented as a single 106 comprises at least processor(s) 108, a digital camera 110, memory 112, and a network interface 128 all of which may communicate with one another by way of a communication bus. In some embodiments, the 3D image acquisition device 106 may include more or fewer components than those illustrated in FIG. 1A.

The network interface 128 may provide connectivity to one or more networks, such as network 126. The processor(s) 108 may thus transmit and receive information and instructions from other computing systems via a network. Processor(s) 108 may include one or more processors or microprocessors and may also communicate to and from memory 112. Processor(s) 108 may provide output information for an optional display (not illustrated) and may also accept input from an optional input device (not illustrated), such as a keyboard, mouse, digital pen, touch screen, etc.

The memory 112 may include computer program instructions that the 3D image acquisition device 106 executes in order to implement one or more embodiments. The memory 112 generally includes RAM, ROM, or other persistent or non-transitory memory. The memory may store the 3D digital images 114 acquired by the digital camera 110. The memory 112 may also store an operating system that provides computer program instructions for use by the processor(s) 108 in the general administration and operation of the 3D image acquisition device 106.

The digital camera 110 is configured to acquire 3D digital images. In an embodiment, the digital camera 110 includes a time-of-flight (TOF) 3D imaging system which is used to acquire a single 3D image. In other embodiments, multiple 2D images from multiple cameras could be used to acquire the 3D image. The TOF 3D imaging system acquires a single point-of-view image by emitting infrared light or radio-frequency modulated light and measuring the delay of the returning light as it is reflected off of the object. A camera lens gathers the reflected light and images it onto a sensor, such as an image sensor comprising an array of pixels. Each pixel can be a photo sensitive element. An example of a photo sensitive element is a photo diode. The delay and the intensity of the returning light are measured for an array of pixels. Each pixel in the array has an amplitude value associated with the intensity that provides brightness information in addition to a value of the distance from the camera to the subject. In the TOF camera the distance corresponds to a phase delay of the frequency modulated illumination and given the constant speed this can be converted to a distance value for each pixel of light. The values can be stored in memory 112. The TOF 3D imaging system may include a TOF component, such as, for example, a TI-OPT8241® by Texas Instruments, Inc., which includes a 320×240 array of pixels. In other embodiments, the array of pixels of the TOF 3D imaging system may include more or fewer pixels.

In an embodiment, the 3D image acquisition device 106 comprises a cell phone, a mobile device, a computer, a laptop, a tablet or the like that comprises a time-of-flight camera 110 or a time-of-flight array. For example, the ZenFone AR® by ASUS is a commercially available cell phone that includes a 3D TOF camera for 3D imaging.

In an embodiment, the image processing and length estimation system 116 receives, via network 126, the 3D image information associated with the snapshot of the subject 104 on the mat 102 that is acquired by the imaging acquisition device 106. For example, the 3D image information includes at least the intensity and distance values generated by the array of pixels. The 3D image information may be referred to as the 3D digital image. The image processing and length estimation system 116 can process the 3D image information to generate a point-cloud representation of the subject 104. The point-cloud is a set of data points in a coordinate system and can represent the external surface of an object. The point-cloud representation of the subject 104 is a set of coordinates that represent the external surface of the subject 104 and is derived from the 3D image information of the subject 104. The image processing and length estimation system 116 can further process the point-cloud representation to generate a pseudo-skeleton of the subject 104. The pseudo-skeleton can also be referred to as a virtual skeleton. The pseudo-skeleton or virtual skeleton represents an approximation of at least a portion of the skeleton of the subject 104 and is derived from the point-cloud representation of the subject 104.

The illustrated image processing and length estimation system 116 comprises at least processor(s) 118, memory 120, display 124, and network interface 138 all of which may communicate with one another by way of a communication bus. In some embodiments, the image processing and length estimation system 116 may include more or fewer components than those illustrated in FIG. 1A. Some components of the image processing and length estimation system 116 may be physical hardware components or implemented in a virtualized environment.

The network interface 138 may provide connectivity to one or more networks, such as network 126. The processor(s) 118 may thus transmit and receive information and instructions from other computing systems via a network. Processor(s) 138 may include one or more processors or microprocessors and may also communicate to and from memory 120. Processor(s) 118 may provide output information for the display 124 and may also accept input from an optional input device (not illustrated), such as a keyboard, mouse, digital pen, etc. The display 124 may be used to display the various stages of the image processing, point-cloud representations, and pseudo-skeletons.

The memory 120 generally includes RAM, ROM, or other persistent or non-transitory memory. The memory 120 may include computer program instructions that the image processing and length estimation system 116 executes in order to implement one or more aspects of the present disclosure. For example, in one embodiment, the memory 120 may include an image processing component 128 comprising computer executable instructions that when executed by the processor(s) 118 cause the image processing and length estimation system 116 to process the 3D digital image to generate a point-cloud; a point-cloud processing component 130 comprising computer executable instructions that when executed by the processor(s) 118 cause the image processing and length estimation system 116 to process the point-cloud to generate a pseudo-skeleton; and a growth determination component 132 comprising computer executable instructions that when executed by the processor(s) 118 cause the image processing and length estimation system 116 to determine an indication growth from a plurality of pseudo-skeletons generated over a period of time.

In addition, memory 120 may store digital images 114. The stored digital images may include the 3D digital images from the 3D image acquisition device 106, various stages of the image processing, point-cloud representations, pseudo-skeletons, and the like. The memory 120 may also store an operating system that provides computer program instructions for use by the processor(s) 118 in the general administration and operation of the image processing and length estimation system 116.

Figure 1B:
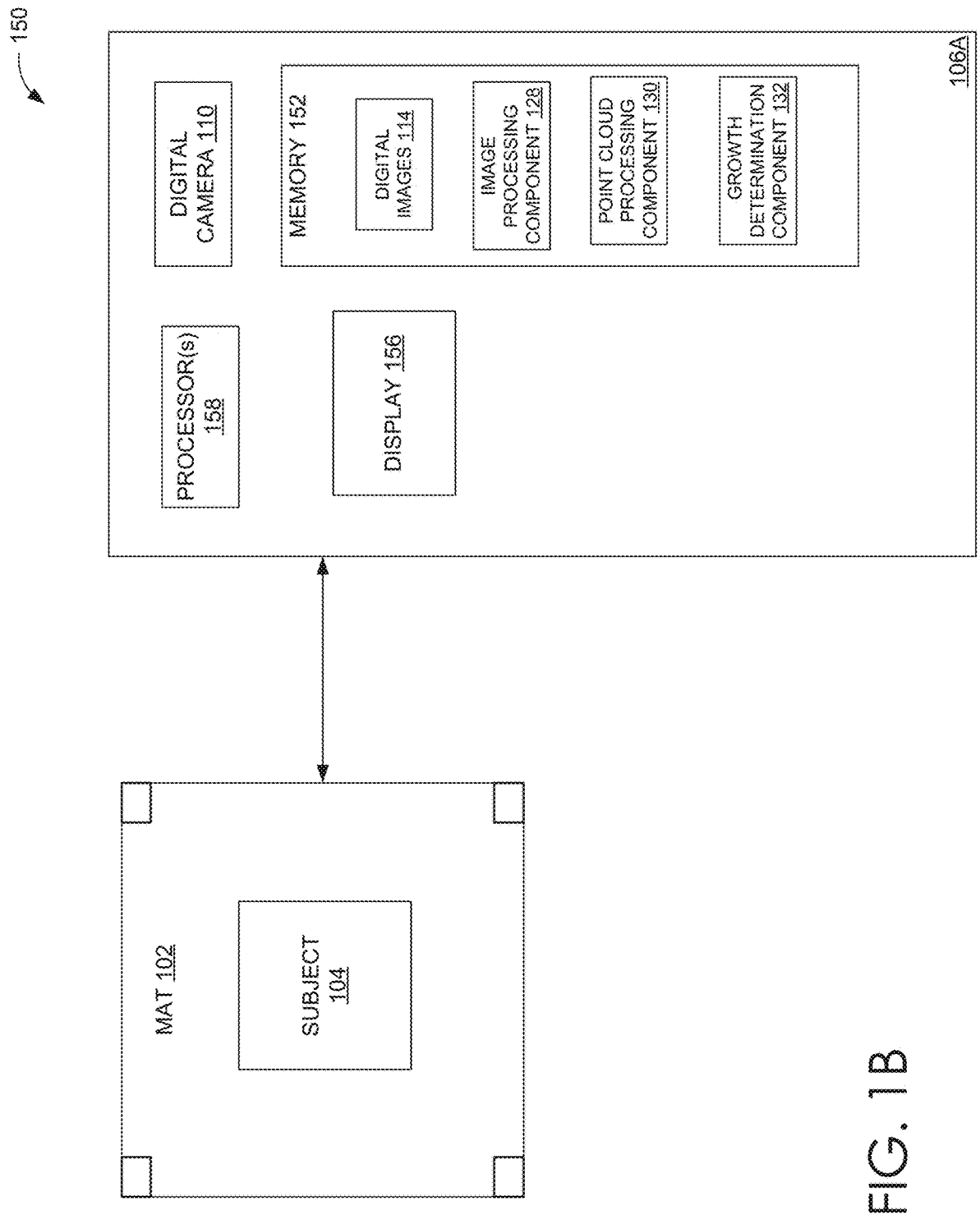
FIG. 1B illustrates a block diagram of another example system to acquire and process 3D digital images of subject to provide an estimate of at least partial length of the subject in a cell phone implementation, according to certain embodiments.

FIG. 1B illustrates a block diagram of another example system 150 to acquire and process 3D digital images of the subject 104 to provide an estimate of at least partial length of the subject 104, according to certain embodiments. The illustrated system 150 comprises the mat 102 and an image acquisition device 106A. The image acquisition device 106A comprises processor(s) 158, display 156, the digital camera 110, and memory 152. In some embodiments, the system 150 may include more or fewer components than those illustrated in FIG. 1B.

Processor(s) 158 are similar to processor(s) 108 and 118 described above and display 156 is similar to display 124 described above. Further memory 152 is similar to memory 112 and 120 described above and can include the digital images 114, the imaging processing component 128, the point-cloud processing component 130, and the growth determination component 132. For example, functionality associated with processor(s) 108 and 118 can also be provided by processor(s) 158, functionality associated with memory 112 and 120 can also be provided by memory 152, and functionality associated with display 124 can also be provided by display 156.

In an embodiment, the image acquisition device 106A is a single device that includes the functionality of the image acquisition device 106 and the functionality of the image processing and length estimation system 116. For example, the image acquisition device 106A can comprise a cell phone or other mobile device that includes the TOF camera, processing functionality, and programming to be able to acquire the 3D digital image of the subject 104 on the mat 102, process the 3D digital image, generate the point-cloud representation, generate the pseudo-skeleton, and determine an estimate of at least the partial length of the subject 104 based on the pseudo-skeleton.

Referring to FIG. 1A, a user, such as a parent, caregiver, clinician or the like, for example, positions the image acquisition device 106 above or in front of the mat 102 having known dimensions. The mat 102 is also referred to as the floor or wall. The user uses the image acquisition device 106 to take a snapshot of the mat 102. The image acquisition device stores the 3D digital image of the mat 102 in the memory 112. In an aspect, the mat 102 is photographed such that the entire mat 102 is captured in the snapshot and in the resulting 3D digital image of the mat 102.

The user also takes a snapshot of the subject 104 on the mat 102. The image acquisition device 106 stores a 3D digital image of the subject 104 on the mat 102 in memory 112. In one embodiment, the subject 104 is placed on the mat 102 in a supine position (lying on one's back), and in another embodiment in front of the mat (standing upright). In some embodiments, the back of the subject's body touches the mat 102 and the subject's arms are at the sides of the body or at a position that does not obscure the subject's torso. Advantageously, the subject is not required to assume an abnormal or uncomfortable posture. Because the subject is not forced into an abnormal or uncomfortable position, the abstract representation of the subject is more replicable and accurate than an abstract representation of the subject acquired by forcing the subject into an abnormal posture.

In an aspect, the subject 104 on the mat 102 is photographed such that the entire mat 102 and the entire subject 104 are captured in the snapshot and in the resulting 3D digital image of the subject 104 on the mat 102. In an embodiment, the body of the subject fills the available frame as much as possible for maximum resolution. In an embodiment, the known height of the digital camera 110 above the subject 104 is approximately at a height of twice the length of the subject 104. Lens optics could be chosen to optimize parameters of distortion versus resolution.

Figure 2:
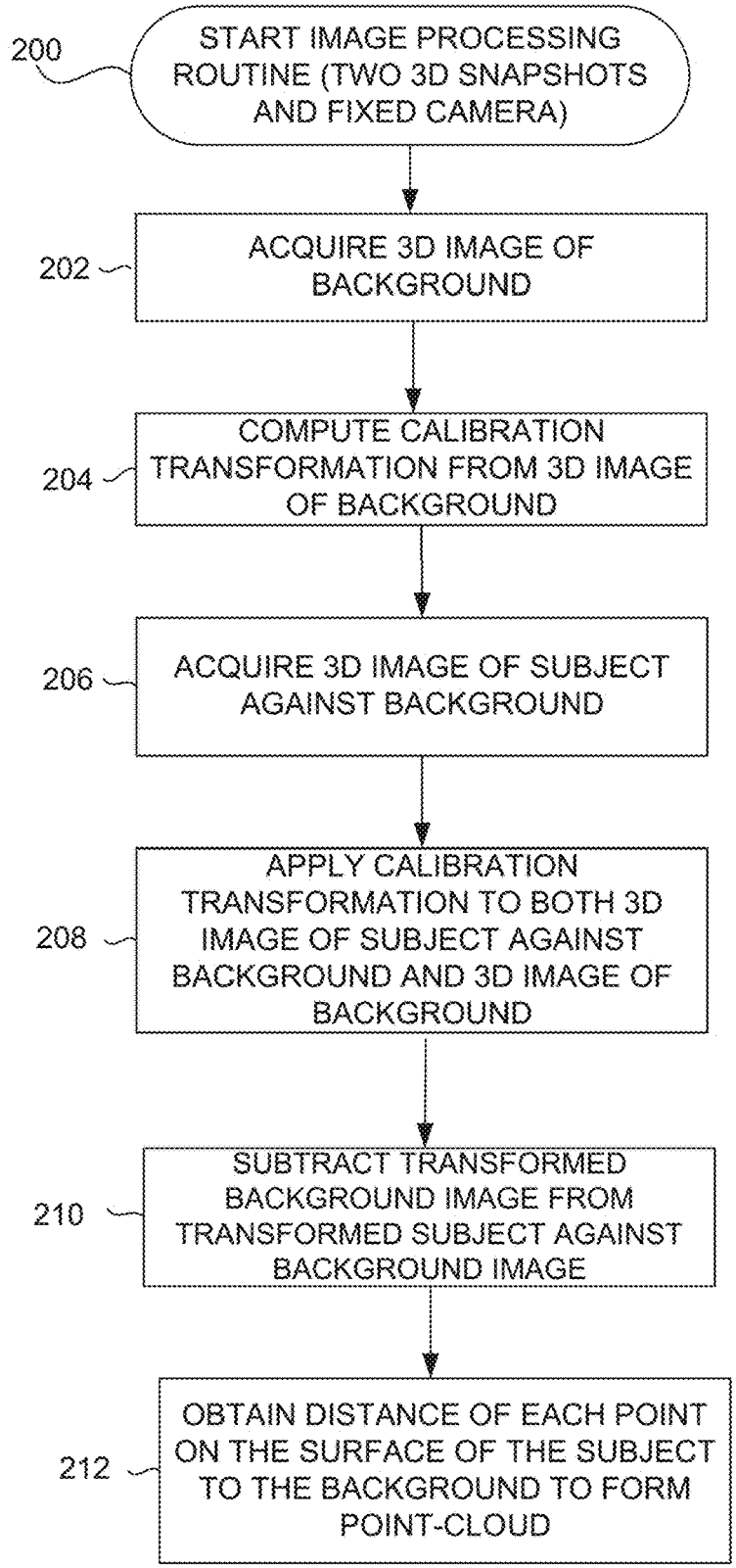
FIG. 2 illustrates a routine to form a point-cloud representation of infant subject using two digital images and fixed camera position, according to certain embodiments.

Turning now to FIG. 2, a routine 200 utilized by the image processing and length estimation system 116 to generate a point-cloud representation of subject using at least two 3D snapshots will be described. Computer algorithms filter and transform the 3D digital image associated with the snapshots of the background and the image of the subject on the background to form a 3D image of the subject. In an embodiment, the transforming modifies the image and filtering smooths the image. In another embodiment, filtering includes determining mathematical derivatives in length and width planes of the image to locate peaks and troughs.

At step 202, the image processing and length estimation system 116 acquires the 3D digital image of the background, such as the mat 102. As described above, the mat 102 is an example of a fixed background that the subject 104 may be placed on or against. For example, the image acquisition device 106 sends the image information associated with the pixel array for the mat 102 to the image processing and length estimation system 116 via the network 126. The 3D digital image of the mat 102 without the subject 104 can be used to calibrate measurements in the X, Y, and Z dimensions. The image of the background, such as the mat 102, may be reused.

The following convention for labeling the three-dimensional form is used: the Y-axis runs from head to toe, the X-axis runs from shoulder to shoulder, and the Z-axis is represented as a distance from the surface of the subject to the to the mat 102, which is also referred to as the floor, for example.

Since the mat is known to be temporally stable and approximately spatially flat, this can be sufficient information to interpolate any point on the floor or wall in three dimensions to desired precision. The 3D digital image of the mat 102 and the known geometry of the scene can then be used in one or more subsequent images to measure the desired distance from each point on the surface of the subject 104 to the nearest point on the floor, along a line perpendicular to the floor.

At step 204, the image processing and length estimation system 116 know the dimensions of the mat and computes a calibration transform that can rotate the entire 3D image such that the camera now accurately positioned on a line perpendicular to the center of the mat 102. After transformation the X and Y scales for the subject surface are then also adjusted to centimeters. After application of this transformation to the composite image, where the composite image is the 3D digital image of the subject 104 on the mat 102, every point in the composite image where the mat 102 is visible also becomes nearly the same constant value. When the two transformed images are then subtracted, the distance values for the mat 102 become nearly zero and all points on the surface of the subject 104 are some positive value of height above the floor. The resulting image is a point-cloud representation of the subject 104. This point-cloud representation is explored for anatomical features.

At step 206, the image processing and length estimation system 116 acquires the 3D digital image of the subject 104 on the mat 102. For example, the image acquisition device 106 sends the image information associated with the pixel array for the subject 104 on the mat 102 to the image processing and length estimation system 116 via the network 126.

Figure 2A:
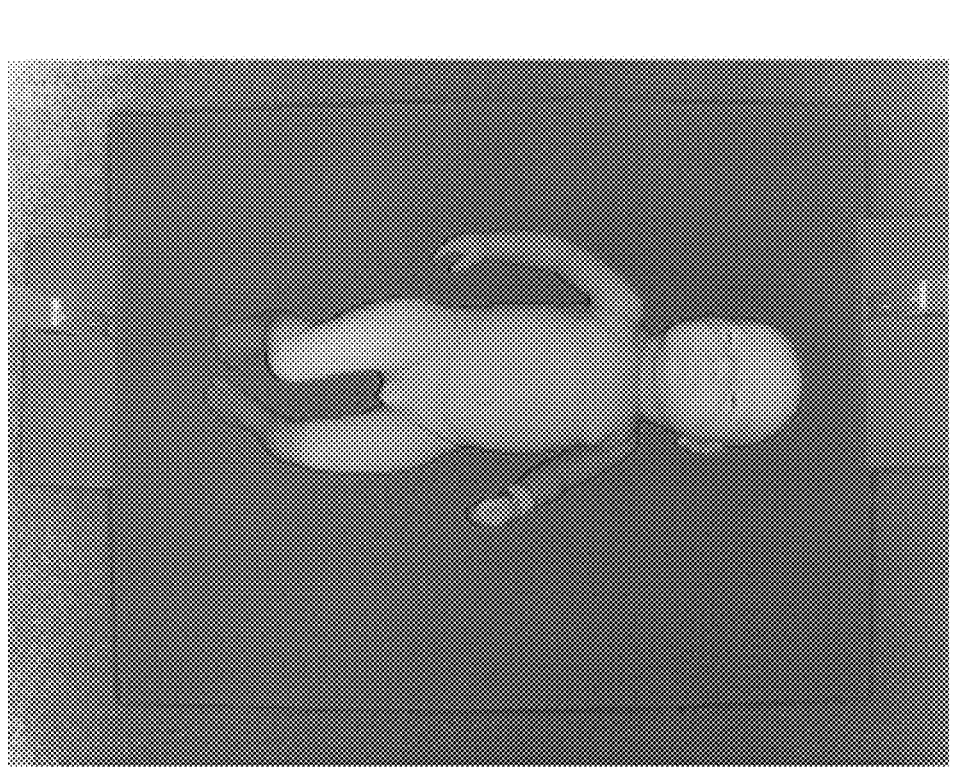
FIG. 2A is an example pictorial representation acquired by the image processing and length estimation system from the image acquisition device of the subject on the background, according to certain embodiments.

FIG. 2A is an example of an image of the subject 104 on the mat 102 acquired by the image processing and length estimation system 116 from the image acquisition device 106.

At step 208, the image processing and length estimation system 116 applies the calibration transformation that was applied to the 3D digital image of the mat 102 to the 3D digital image of the subject 104 on the mat 102. As described above, after application of the calibration transformation to the 3D digital image of the subject 104 on the mat 102, points in the transformed image of the subject 104 on the mat 102 where the mat 102 is visible also become nearly the same constant value. In another embodiment, a different calibration transformation is applied to the 3D digital image of the subject 104 on the mat 102 than is applied to the 3D digital image of the mat 102.

At step 210, the image processing and length estimation system 116 transforms the image data by subtracting the transformed image data for the mat 102 from the transformed image data for the subject 104 on the mat 102.

In another embodiment, the 3D digital image of the mat 102 is acquired once, transformed, and stored in memory 120. Routine 200 subtracts the same stored, transformed image of the mat 102 from the transformed image data for the subject 104 on the mat 102 for multiple 3D digital images of the subject 104 on the mat 102 acquired over time.

At step 212, the image processing and length estimation system 116 obtains the distance of each point of the surface of the subject 104 to the floor from the subtraction. When the two images are subtracted, the distance values for the mat 102 become nearly zero and points on the surface of the subject are positive values with respect to the floor.

Figure 2B:
FIG. 2B an example pictorial representation of an example transformed image of the subject represented by the distance of each point of the surface of the subject to the floor, according to certain embodiments.

FIG. 2B is an example transformed image 630 of the subject 104 represented by the distance of each point of the surface of the subject to the floor. Image 630 represents a point-cloud describing the surface of the subject's body. The points of the point-cloud are vertices of a convex mesh restricted to a two-dimensional hypersurface. Each vertex is referenced to a corresponding point on the floor. As described in further detail below, anatomical features or natural landmarks of the subject 104 are placed on the point-cloud representation of the subject 104.

Figure 3:
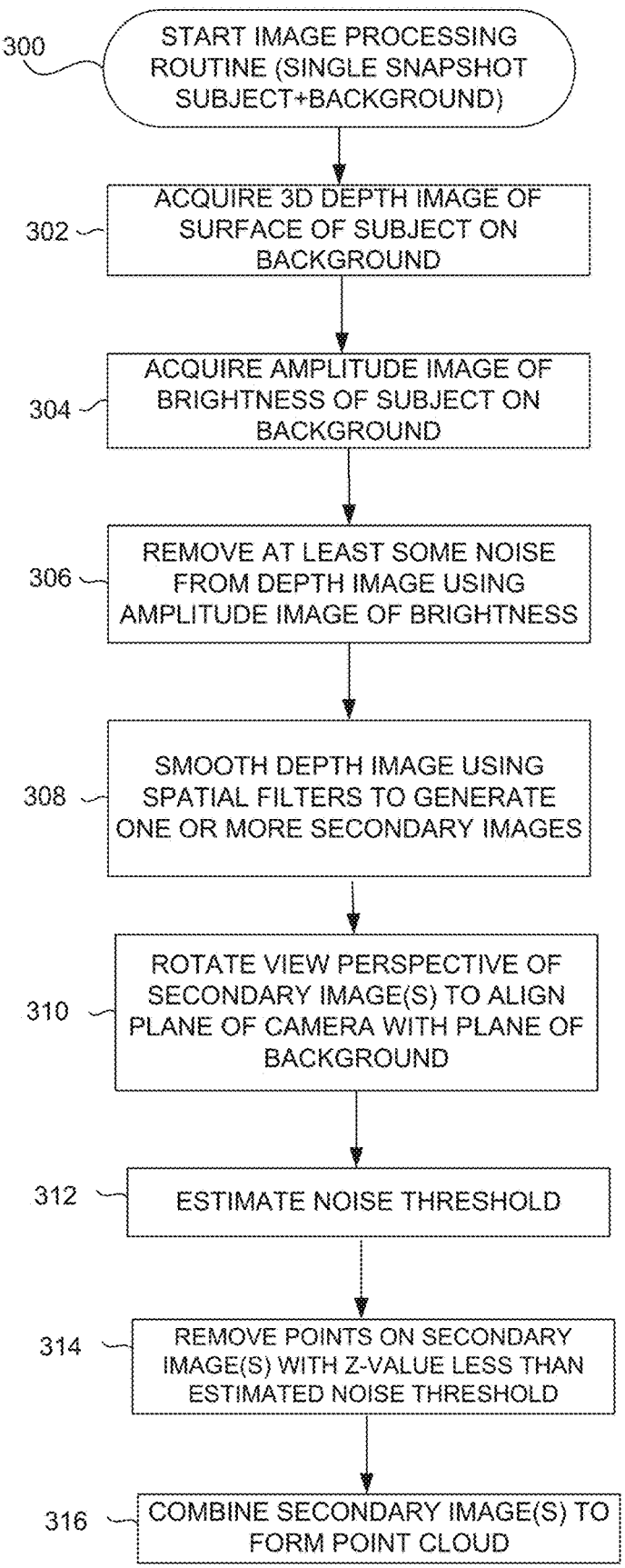
FIG. 3 illustrates a routine to form a point-cloud representation of an infant using a single 3D digital image of the subject, according to certain embodiments.

Turning now to FIG. 3, a routine 300 utilized by the image processing and length estimation system 116 to generate a point-cloud representation of an subject using a single snapshot will be described. Taking a single snapshot of the subject 104 on the mat 102, instead of also needing to photograph the mat 102 alone, makes it much easier and convenient for parents or other caregivers to photograph the subject frequently, such as daily. As described above, the mat 102 is an example of a fixed background that the subject 104 may be placed on or against.

The user, such as the parent or other caregiver takes a snapshot of the subject 104 on the mat 102 without taking a snapshot of the mat 102 alone. The snapshot of the subject 104 on the mat 102 results in a 3D digital image of the subject 104 on the mat 102 stored in memory 112. As described above, the subject 104 can be placed on the mat 102 in a supine position, with the back of the subject's body touching the mat 102 and the subject's arms laying the sides of the body or at a position that does not obscure the subject's torso. Advantageously, the subject is not required to assume an abnormal or uncomfortable posture. Because the subject is not forced into an abnormal or uncomfortable position, the abstract representation of the subject is more replicable and accurate than an abstract representation of the subject acquired by forcing the subject into an abnormal posture.

At step 302, the image processing and length estimation system 116 acquires the distance values associated with depth information for the 3D digital image of the subject 104 on the mat 102. In an embodiment, the image processing and length estimation system 116 acquires the distance values from the image acquisition device 106, via network 126. Mat 102 has known dimensions and observable corners.

At step 304, the image processing and length estimation system 116 acquires the amplitude values associated with brightness information of the reflected light for the 3D digital image by the subject 104 on the mat 102. In an embodiment, the image processing and length estimation system 116 acquires the amplitude values from the image acquisition device 106, via network 126.

For example, the TOF camera 110 stores an amplitude value that provides brightness information associated with the returning light and a distance value that provides depth information for each snapshot. The image acquisition device 106 can send the amplitude and distance values associated with the pixel array for subject 104 on the mat 102 snapshot to the image processing and length estimation system 116 via the network 126. The array of amplitude values can be characterized as an amplitude image associated with brightness and the array of distance values can be characterized as a depth image.

Figure 3A:
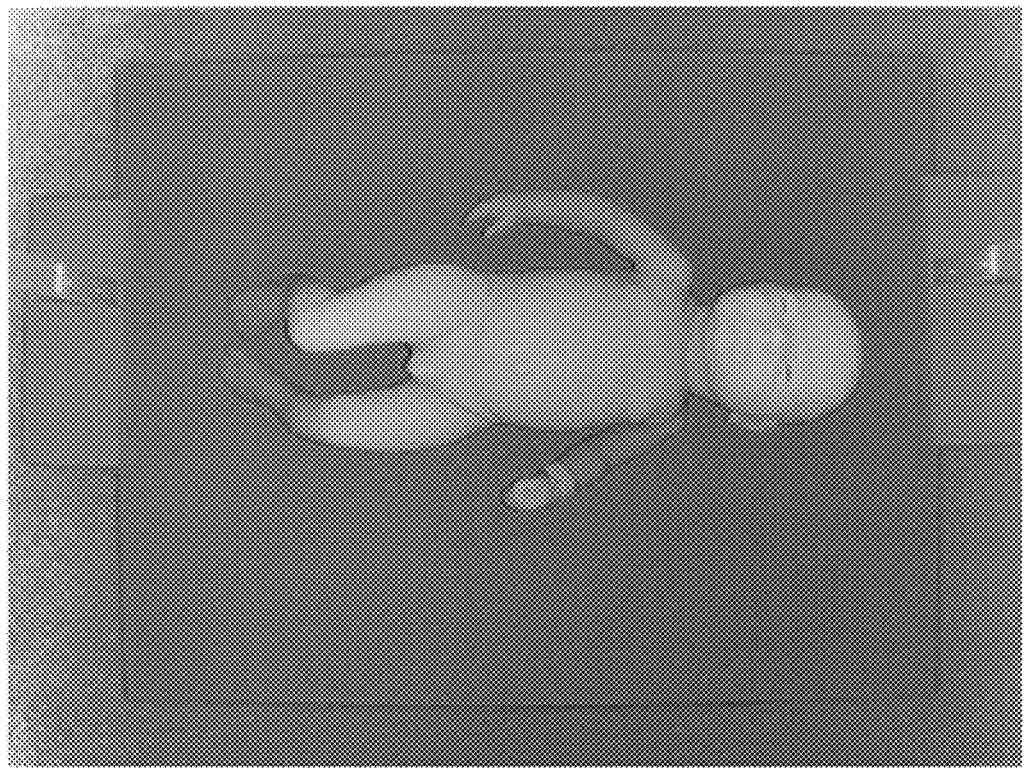
FIG. 3A is an example pictorial representation of a depth image of the subject on the background, according to certain embodiments.
Figure 3B:
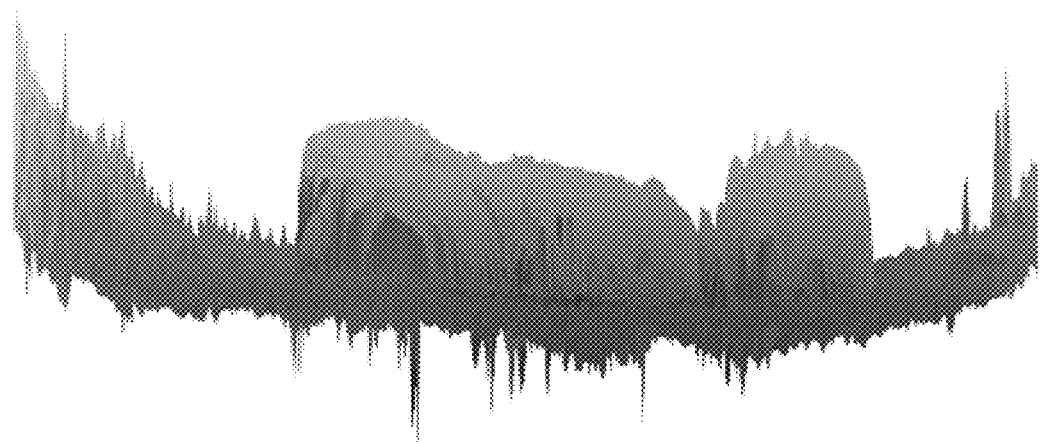
FIG. 3B is an example pictorial representation of the depth image of FIG. 3A rotated to horizontal, according to certain embodiments.
Figure 3C:
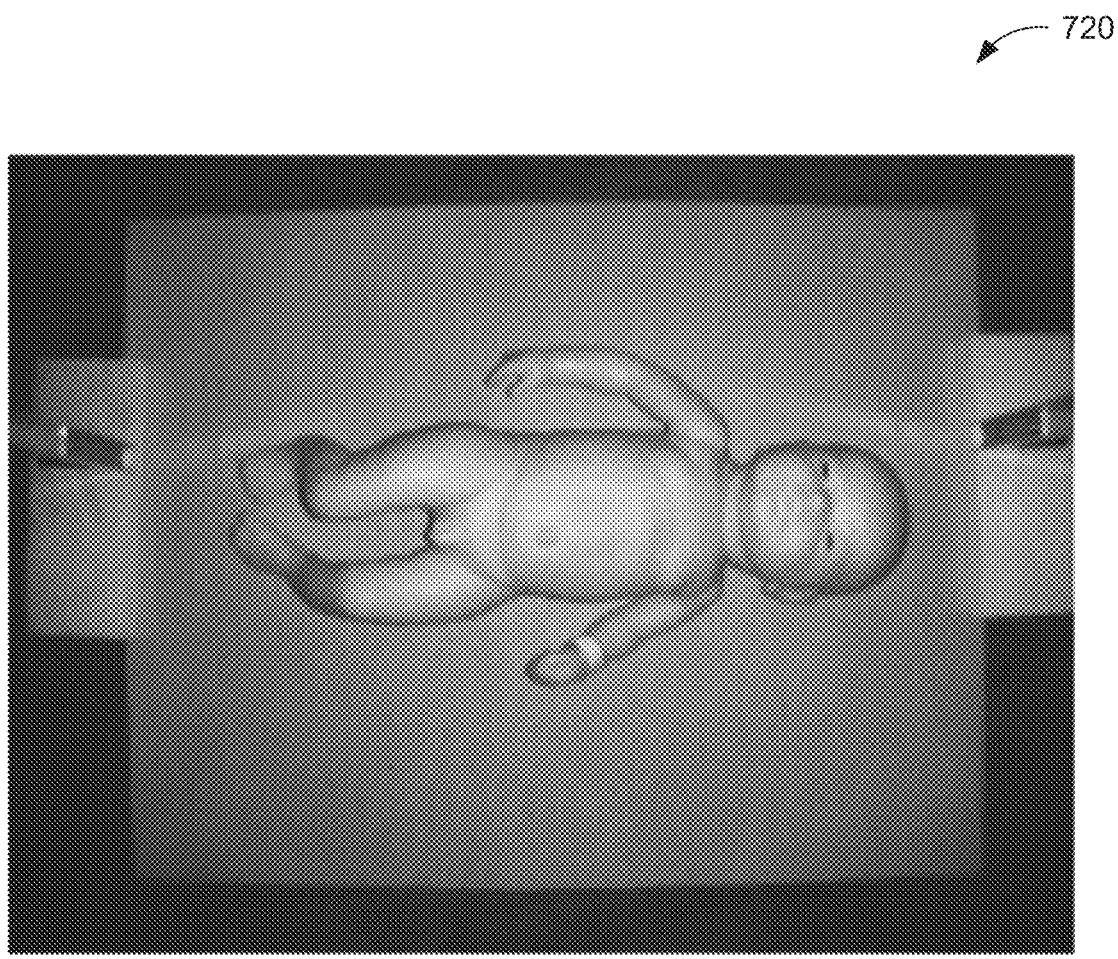
FIG. 3C is an example pictorial representation of an amplitude image of the subject on the background, according to certain embodiments

FIG. 3A is an example 3D depth image 710 of the subject 104 on the mat 102. The 3D depth image 710 can also be referred to as the phase image 710. When the 3D depth image 710 is rotated to horizontal, as illustrated by example image 730 in FIG. 3B, the height of the points on the surface of the subject 104 above the floor are shown. FIG. 3C is an example amplitude image 720 of the subject 104 on the mat 102. The amplitude image 720 can also be referred to as the intensity image 720. The each Z dimension along the Z-axis in the amplitude image 720 represents the brightness of the corresponding pixel in the pixel array.

At step 306, the image processing and length estimation system 116 uses the amplitude image 720 to remove at least a portion of the noise and/or reflections from the depth image 710. This is accomplished by detecting and replacing outlier pixels and smoothing with a Gaussian kernel.

At step 308, the image processing and length estimation system 116 applies one or more smoothing algorithms to the depth image 710 to generate one or more secondary images. In an embodiment, the image processing and length estimation system 116 applies one or more spatial filters to the depth image 710 to generate the secondary images. In an embodiment, the secondary images are different versions of the depth image 710, where each version has a different amount of smoothing or filtering. The image processing and length estimation system 116 can store the secondary images in the memory 120. The smoothing filters were Gaussian and in addition a single median filter was used to replace outlier pixels in the real images.

Calibration information can be derived from the edges of the mat 102. At step 310, the image processing and length estimation system 116 can rotate the view perspective of the secondary images so that resulting rotated images represent the digital camera 110 appearing in virtual space directly above the mat 102. For example, the image processing and length estimation system 116 can detect the mat edges. In an embodiment, the corners of the mat 102 are detected. After detecting the mat edges, the image processing and length estimation system 116 can rotate the secondary images to flat and rectangular, and can scale the secondary images to the known dimensions of the mat 102.

The virtual plane of the digital camera 110 is aligned with the mat 102 in the rotated images. In the rotated secondary images, the approximately all of the depth values for the mat 102 are approximately a constant value plus noise. This value is then subtracted from the composite 3D image.

Figure 3D:
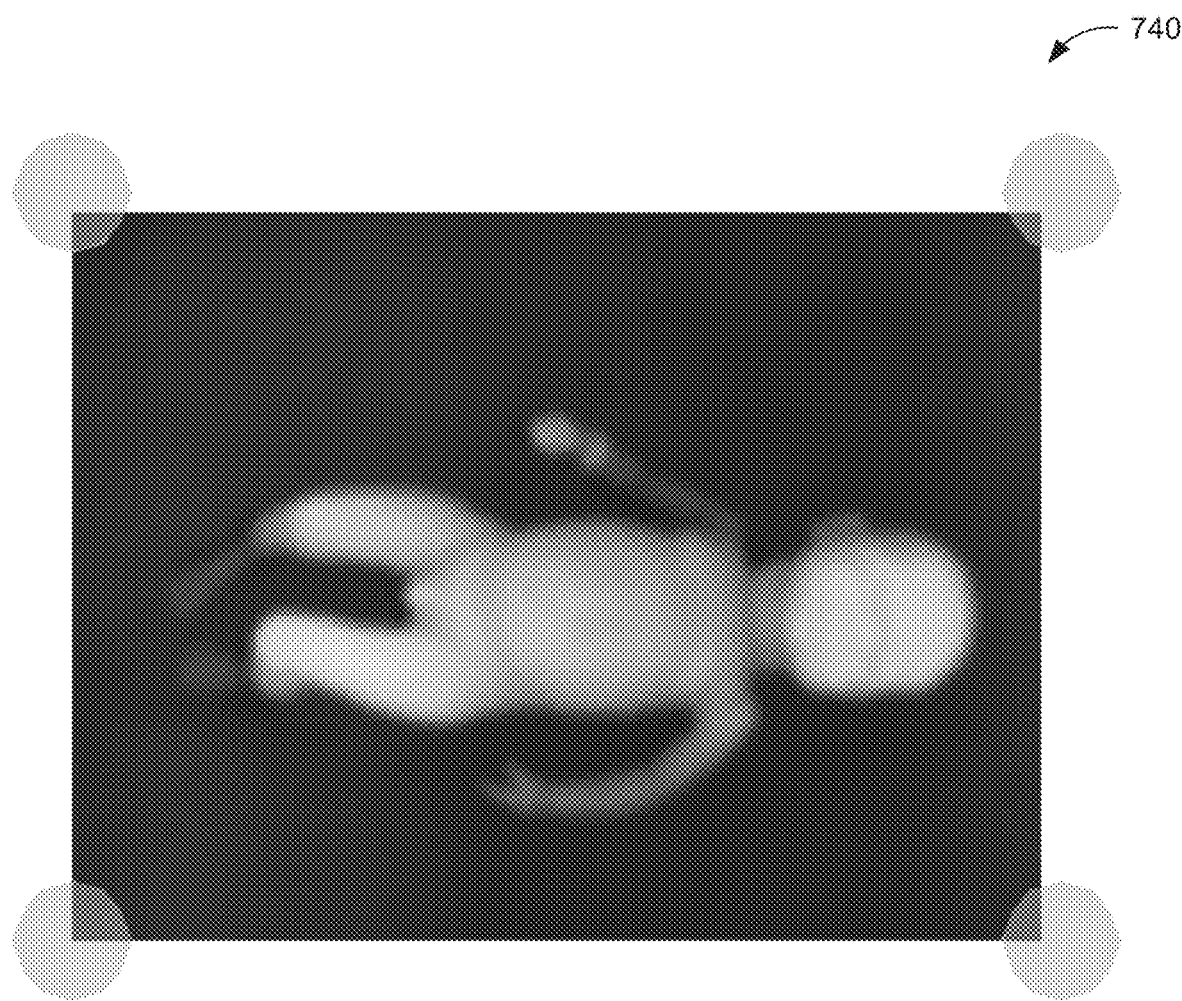
FIGS. 3D and 3E are example pictorial representations of transformed images of the subject representing the surface of the subject's body, according to certain embodiments.
Figure 3E:
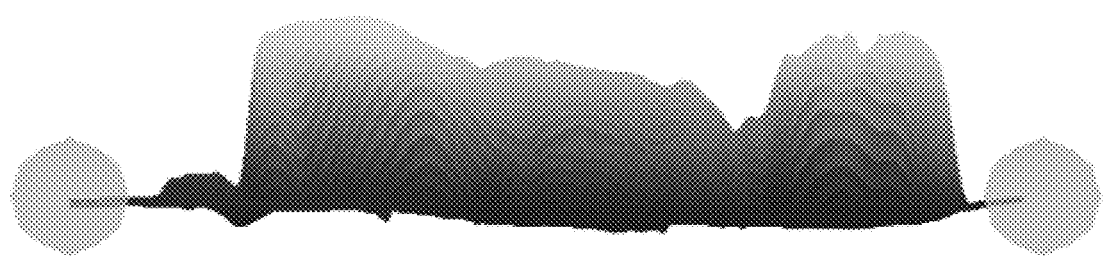

FIGS. 3D and 3E are example transformed images of the subject representing the surface of the subject's body. FIG. 3D illustrates an example image 740 with detected mat corners that has been rotated to be flat and rectangular and scaled according to the known mat dimensions. FIG. 3E illustrates an example image 750 of the flat, rectangular, and scaled image 740 visualized along the Y-axis. Horizontal image 750 shows the depth information along the Z-axis.

At step 312, the image processing and length estimation system 116 estimates the noise threshold of the noise. This noise threshold is derived from the variation of background which now is variation about zero. For example, if this is 1 cm, then all points with Z values lower than 1 cm are removed in the original surface leaving only points on the frontal surface of the subject.

At step 314, the image processing and length estimation system 116 process the secondary images by removing the mat 102 from the rotated secondary images. The image processing and length estimation system 116 removes the mat 102 from the rotated secondary images by deleting the points in the secondary images having a Z (height) value that is less than the estimated noise threshold. In an embodiment, the image processing and length estimation system 116 removes the mat 102 from the rotated secondary images by deleting the points in the secondary images having a Z value that is less than the constant value plus estimated noise threshold.

After rotation, there is no longer a fixed relationship between the camera pixels of the acquired 3D digital image and the points of the rotated secondary images. In an embodiment, the points of the rotated secondary images represent vertices of a mesh over a surface of the subject.

At step 316, the image processing and length estimation system 116 combines data from one or more of the processed secondary images to form a point-cloud representation of the subject 104. Data from the processed secondary images are combined to provide multiple Z values for the points on the point-cloud representation having auxiliary information about brightness and surface curvature. The smoothing filters were optimized based on the relative size of the different anatomical landmarks.

Figure 3F:
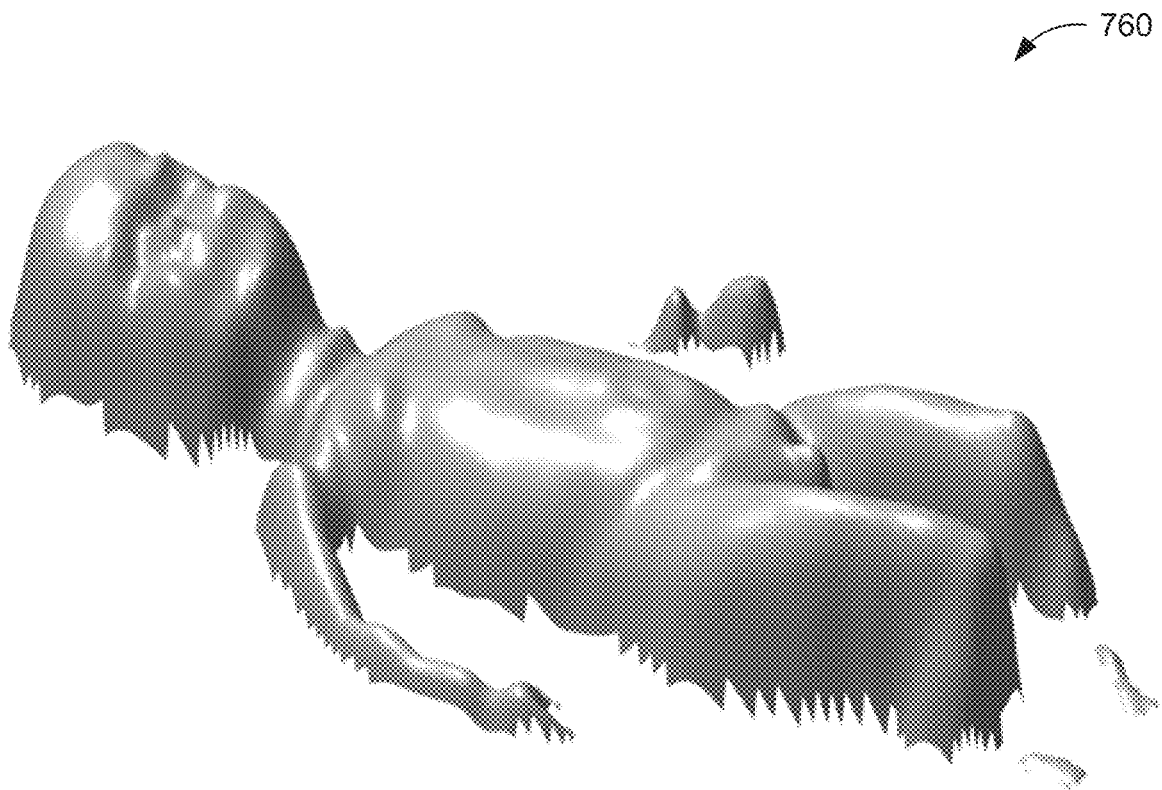
FIG. 3F is an example pictorial representation of a surface mesh representation of the subject, according to certain embodiments.

FIG. 3F illustrates an example image 760 of the point-cloud representation of the subject 104. In an embodiment, the point-cloud representation is a noise free or approximately noise free mesh surface approximation of the subject 104.

Figure 4:
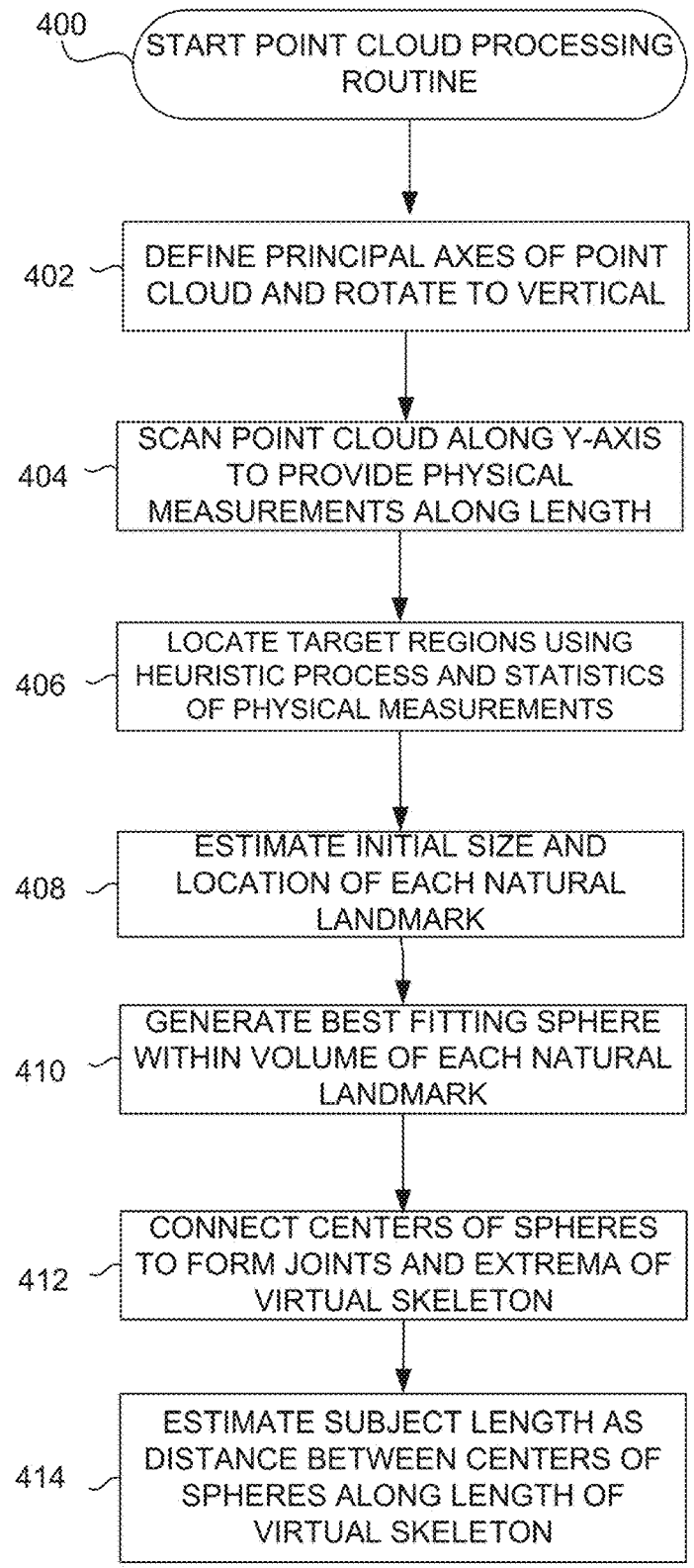
FIG. 4 illustrates a routine to generate a pseudo-skeleton of an infant, according to certain embodiments.

Turning now to FIG. 4, a routine 400 to estimate the length or partial length of the subject from a generated pseudo-skeleton of the subject 104 will be discussed. The estimation of length begins with the computation of the principal axes of the points on the surface image of the subject 104. As described above, the following convention for labeling the three-dimensional form is used: the Y-axis runs from head to toe, the X-axis runs from shoulder to shoulder, and the Z-axis is represented as a distance from the surface of the subject to the floor.

At step 402, the image processing and length estimation system 116 computes the principal axes of the point-cloud. In an embodiment, the image processing and length estimation system 116 further rotates the point-cloud representation to vertical. This provides a definition of the principal axes of the point-cloud representation of the subject 104. The longest axis is orientated through the volume of the subject surface so that the representation of the subject 104 is aligned with the Y-axis of the measurement frame. The point (0, 0, and 0) is defined as $Z_0$. In an embodiment, $Z_0$ is located at the intersection of the Y-axis with the longest axis across the volume of the subject surface (defined as the X-axis).

Figure 4A:
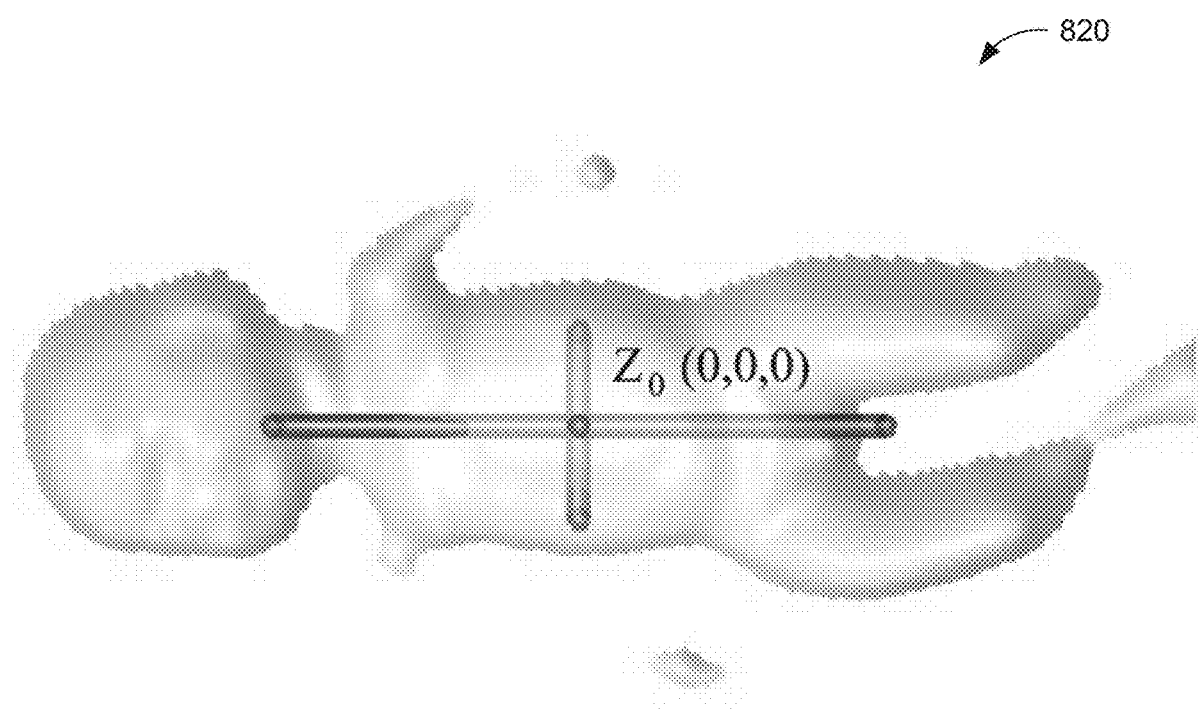
FIG. 4A is an example pictorial representation of a point-cloud representation showing the Y-axis, the X-axis, and Z=0, according to certain embodiments.

FIG. 4A illustrates an example cloud point representation 820 showing the Y-axis, the X-axis, and $Z_0$. In the example point-cloud representation, the X-axis is located approximately mid-way along the torso of the subject 104.

At step 404, the image processing and length estimation system 116 scans the point-cloud representation along the Y-axis to provide physical measurements along the length. Further, the image processing and length estimation system 116 filters the point-cloud representation to refine the image and to locate peaks and troughs. FIGS. 3D and 3E illustrate examples of filtered images 740 and 750, respectively. Several different Gaussian smoothing spatial integration used by filters assist detection of known anatomical features i.e. the peak of the forehead by smoothing the head so that a clear convex surface is always produced even in the presence of a small spot or ridge.

At step 406, the image processing and length estimation system 116 processes the filtered image to locate natural landmarks of the subject's anatomy on the image. In an aspect, the image processing and length estimation system 116 locates target regions of the natural landmarks using heuristic processes and statistics of the physical measurements. Examples of natural landmarks include, but are not limited to the eyes, navel, neck, knees, hip, ankle, heel, top of head, bottom of feet, arms, wrist, elbow, shoulder, centroid of the head, and the like.

Advantageously, the use of natural landmarks can be reliably replicated in subsequent images of the subject 104 and do not require the same posture of the subject 104 for each image. This is different from the need to measure absolute height (i.e. from the top of the head to the heel in a standing or supine position), which requires the same posture for each observation. Because the natural landmarks can be reliably replicated in subsequent images, and can be used to create the pseudo-skeleton of the infant, indications of growth can be determined by the change in the length between the natural landmarks as images are acquired over time (if they are independent of postural variation). For example, the distance from a point midway between the eyes and the average of the distance to each knee can be determined in each of a series of 3D images taken over time. As the infant grows, the increase in this distance (or partial length) is proportional to the overall growth of the subject. In other words, the partial length determined by the difference of the distance between first and second natural landmarks can be compared for the observation acquired at a first point in time to the partial length (the distance between the same first and second natural landmarks) acquired at a later point in time, and the change on the partial length provides an indication of the growth of the subject over the time between the two observations.

The use of natural landmarks avoids the use of indeterminate position of locations. The top of the head that may have more or less hair and irregular form, making the exact location of the top of the head difficult to determine. Further, soft and flexible anatomy, such as the bottoms of the feet, may result in non-repeatable or ambiguous measurements. A model head or model feet may be generated used to locate the positions that could be used along with the pseudo-skeleton to obtain the absolute length without having to position the subject by aligning the head and stretching the legs.

At step 408, the image processing and length estimation system 116 estimates the initial size and location of each natural landmark. In an embodiment, the image processing and length estimation system 116 uses a feature detection algorithm to compute a general estimate of size or volume of the filtered image. The estimate of the size or volume can provide calibration information for detecting features of the subject 104 on the point-cloud representation. For example, the estimated volume permits the image processing and length estimation system 116 to estimate the relative volume and curvature for each class of anatomical features or natural landmarks that are used to estimate the skeletal structure of the subject 104. Volume estimates are possible because the algorithm actually does produce a closed volume with the frontal surface reflecting the true surface of the subject. Although the back surface is assumed flat, there is not a lot of residual volume in this method. Although it is always somewhat larger than the true volume, this estimate will replicate well for repeated measurements.

Random error is reduced in the algorithm overall because of the method used to fit spherical point-clouds to the interior of this volume. A general knowledge of anatomy allows us to select a region of the body as shown in FIG. 6a, 6B that would contain a joint. This is viewed as point-cloud band around the torso and each leg as a general constraint over the length. A sphere is created with a radius estimating the interior volume. This is also guide by the heuristic component that knows the knees may be up in the air but assumes hips are on the floor. Each sphere is then snugly fit as closely as possible in the interior of the surface mesh using a simplified point set regression.

Once the feature detection algorithm estimates the general surface of the physical form, the feature algorithm can distinguish landmarks along its length like the bifurcation of the legs at one end of the torso. Successive filters with various kernels are applied to the 3D data of points on the body that are optimized for anatomical features and natural landmarks, such as, but not limited to:
 a. Head, Head
 b. Neck, Chest
 c. Hips, Thighs
 d. Knees, Calves
 e. Ankles, Feet In an embodiment, methods using one or more heuristic algorithms can be used to identify the natural landmarks. An embodiment of a heuristic algorithm may comprises the following measurements:
 i. Detect the orientation of the longest axis of the subject's body, Y axis;
 ii. Scanning along this axis all points within a specified range of Y coordinates define a band of points around the torso at every multiple of some length resolution (for example, a parameter set to 1% of length).
 iii. Each band is comprised of a number of points on the upper surface of the subject;
 iv. Each band also contains an equal number of points on the inferior surface with the same X and Y values and a Z value of zero.
 v. Hence, there is now a closed volume defined at each segment of length and it can be associated with a number of measures:
   a. Volume of segment
   b. The minimum and maximum range of X, Y, Z.

c. The associated centroids center of mass.
d. In the X axis or width, sub-centroids are computed of the remaining volumes on left and right side of the center.

In an embodiment, methods using the measurements described above and a heuristic algorithm can be used to identify natural landmarks as extrema and points of articulation along the length of the subject. The first heuristic may assume the range for identification of all features for length computation lies between the first and last segments defined above. These landmarks may be accurately estimated as follows:

i. NECK: The neck segment is identified as the minimum volume segment. This also identifies which end of the body contains the head.
ii. FOREHEAD: Scanning now from the first segment, the forehead segment is the first volume maximum.
iii. HIPS: Continuing this scan, the first point of bifurcation, the top of legs, is defined when Z maxima of sub-centroids exceed Z maximum of total centroid. The hip segment is the last maximum in width prior to this point. The X axis volume centroid divides this segment into left and right hip segments.
iv. KNEES: Are detected as a variation in cross section For example, there may not be a clear neck feature in a view of a chubby infant but a centroid of the diminished mass between head and torso would be detectable and sufficient to locate the neck joint used for the model. An estimate of overall length does not vary significantly if the neck is approximated by a single joint between head and torso rather than defined by the seven vertebrae of realistic anatomy.

At step 410, the image processing and length estimation system 116 generates a sphere within a volume of each natural landmark. In an embodiment, the image processing and length estimation system 116 generates the best fitting sphere, where the volume of the sphere closely matches the volume of the natural landmark.

At step 412, the image processing and length estimation system 116 connects vertices of the spheres to visualize pseudo-joints and extrema of a virtual skeleton on the image. The virtual skeleton can also be referred to as a pseudo-skeleton. The spheres placed in the image are sized to correspond to the volume of the individual landmark. For example, the sphere located at the infant's hip is larger than the sphere located at the infant's knee. The set of pseudo-joints may differ in number from image to image, but for a given 3D digital image there will be enough to estimate the small number of vertices required for a virtual skeleton.

Figure 4B:
FIGS. 4B-4G illustrate example pseudo-skeletons with spherical representations of natural landmarks, according to certain embodiments.
Figure 4C:
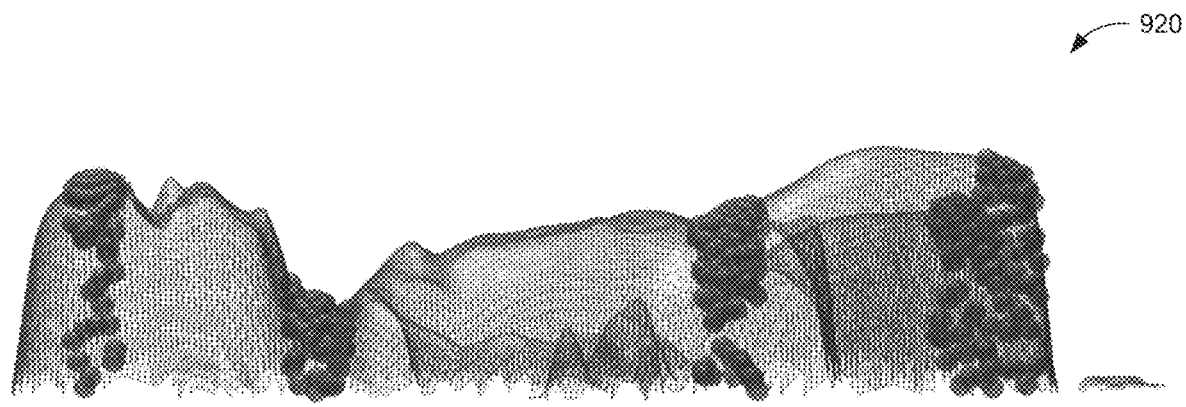

FIG. 4B illustrates an example of a computer-generated side view 910 of a virtual skeleton. FIG. 4C illustrates an example of a computer-generated top view 920 of a virtual skeleton. The views 910, 920 of the virtual skeleton indicate the locations of the eyes, neck, pelvic joints, and knees.

Figure 4D:
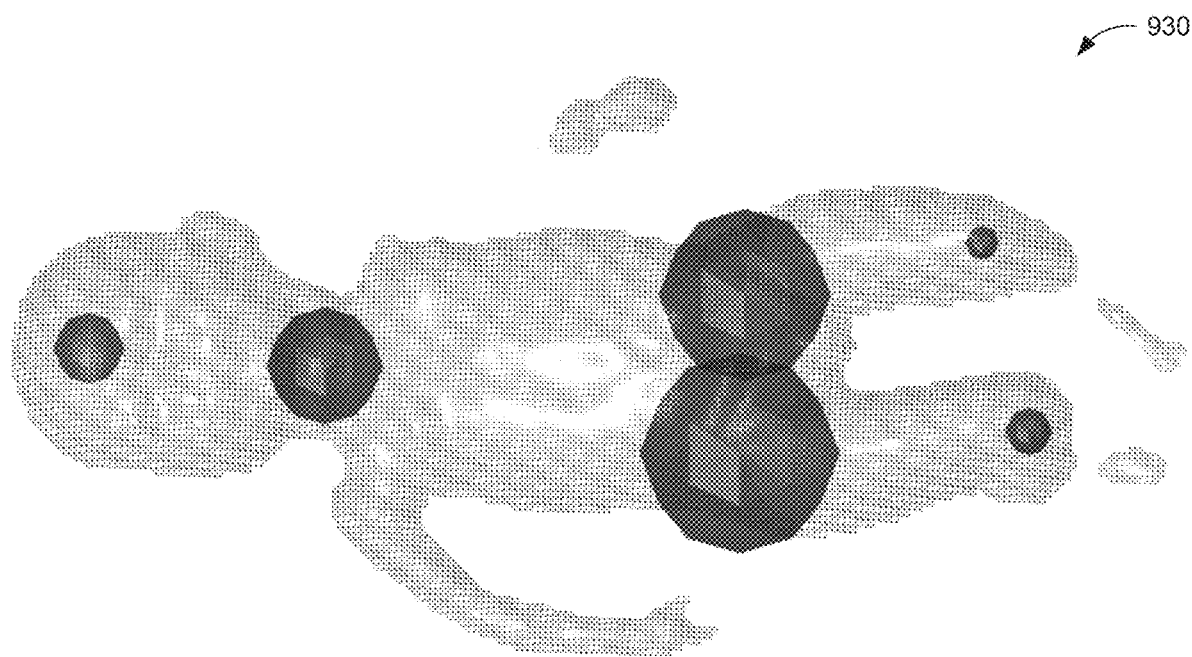
Figure 4E:
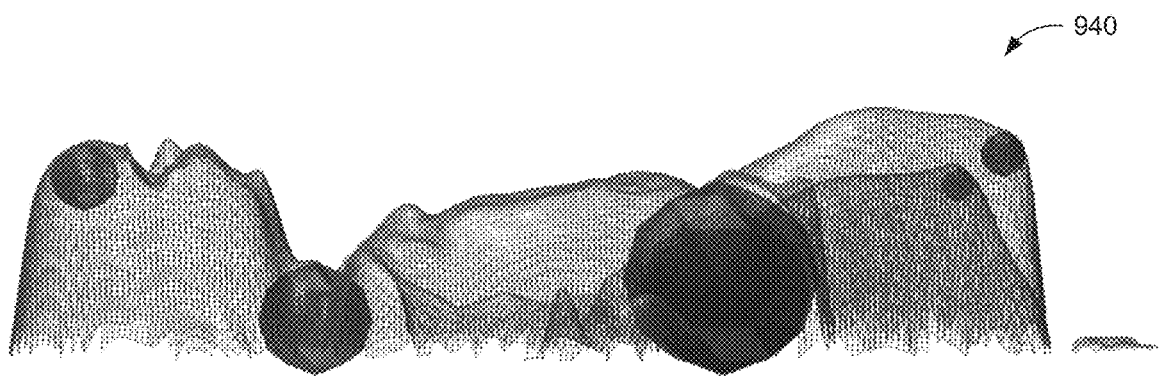

FIG. 4D illustrates an example of a side view 930 of a 3D image of the subject 104 including the virtual skeleton of FIG. 4B. FIG. 4E illustrates an example of a top view 940 of a 3D image of the subject 104 including the virtual skeleton of FIG. 4C. FIGS. 4D and 4E further illustrate the depth information provided by a single frame from a TOF camera.

Figure 4F:
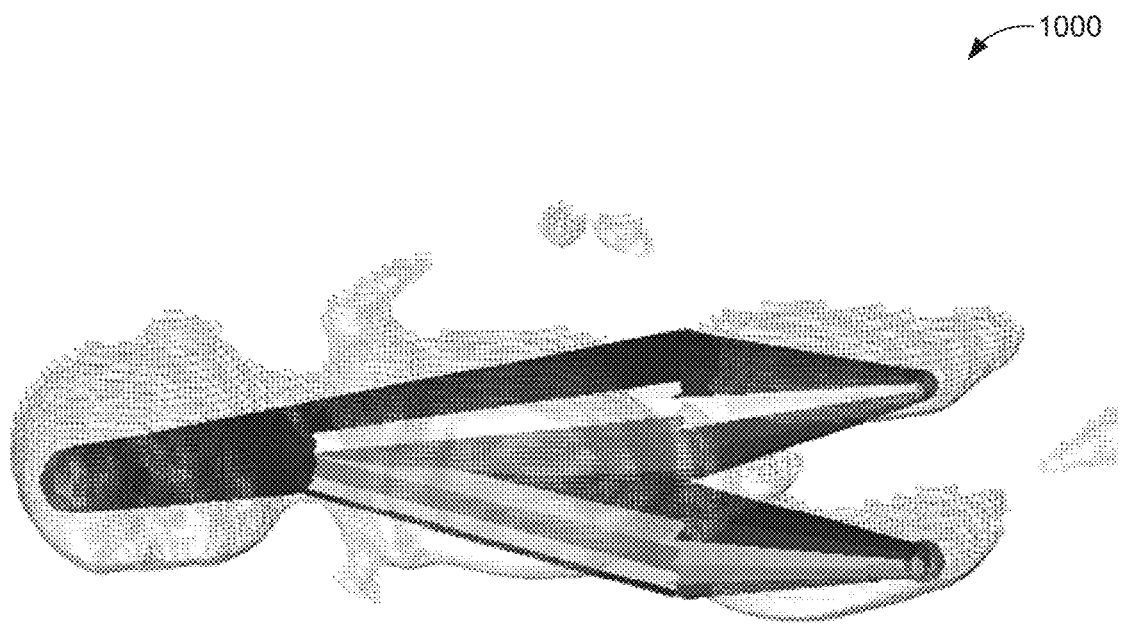
Figure 4G:
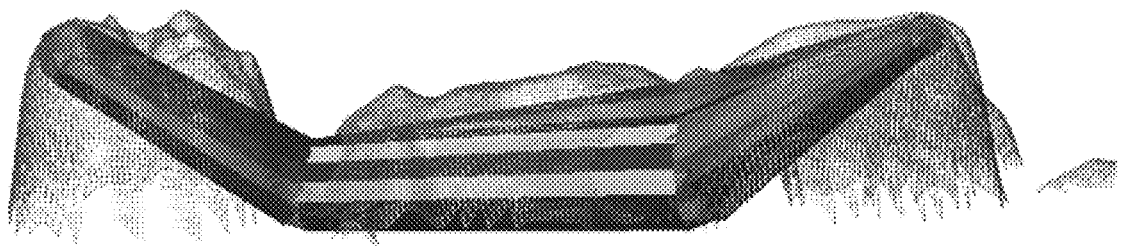

FIGS. 4F and 4G illustrate other examples of computer-generated virtual skeletons 1000, 1010. FIG. 4F illustrates a top-view 1000 and FIG. 4G illustrates a side-view 1010.

At step 414, the image processing and length estimation system 116 estimates the length of the subject as the distances between the centers of the spheres for selected portions of the virtual skeleton. The cumulative distances along the Y-axis, from one pseudo-joint to the next, provides an estimate of the length of the subject 104. In some embodiments, the image processing and length estimation system 116 determines the total overall length of the subject 104. In other embodiments, the image processing and length estimation system 116 determines a partial length of the subject 104. For example, the distance between the neck and the hips, the distance between the hips and the knees, the distance between the neck and the knees, or any other partial length of the subject 104 or any combination of partial lengths can be used to provide an indication of the growth of the subject 104.

Figure 5:
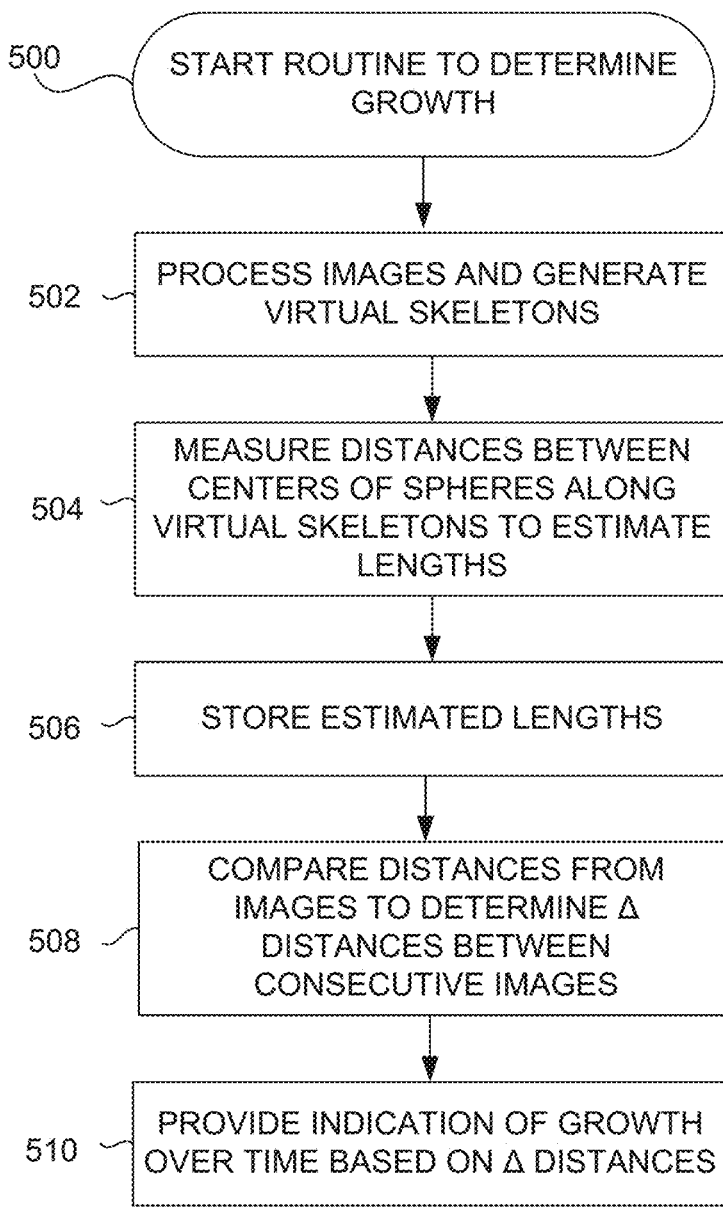
FIG. 5 illustrates a routine to provide an indication of growth, according to certain embodiments.

Turning now to FIG. 5, a routine 500 to provide indication of growth will be described. At step 502, the image processing and length estimation system 116 acquires and processes the 3D digital images of the subject 104 on the mat 102. The 3D digital images can be received periodically. In an embodiment, the period between receiving consecutive 3D digital images is short so as to distinguish the infant's growth between saltations and stasis. Examples of short periods between receiving consecutive 3D digital images of the subject 104 on the mat 102 are daily, weekly, monthly, hourly, every 12 hours, 4 times a day, twice a day, and the like. In an embodiment, the 3D digital images are processed according to embodiments described with respect to FIG. 2. In another embodiment, the 3D digital images are processed according to embodiments described with respect to FIG. 3. The image processing and length estimation system 116 further generates virtual skeletons from the processed images. In an embodiment, the virtual skeleton is generated according to embodiments described with respect to FIG. 4.

At step 504, the image processing and length estimation system 116 determines estimates of length or estimates of partial length by measuring the distances between the spheres in one or more portions of the virtual skeletons for each processed image. The cumulative distances between the spheres in the one or more portions of the virtual skeletons provides estimates of the subject's length or partial length.

At step 506, the image processing and length estimation system 116 stores the estimates of the subject's length or partial length.

At step 508, the image processing and length estimation system 116 compares the cumulative distances from the processed images (i.e., the estimates of the subject's length or partial length) to determine a change in the subject's length or partial length over time. For example, a first estimate of subject length from a first 3D digital image is compared to a next estimate of subject length from a next 3D digital image, taken later in time than for first 3D digital image. The change in estimated subject length between successive measurements over time provides an indication of growth. The indication of growth may be compared with normal growth to determine if the subject's growth is normal and to provide timely intervention when the subject's growth is faltering.

Figure 6:
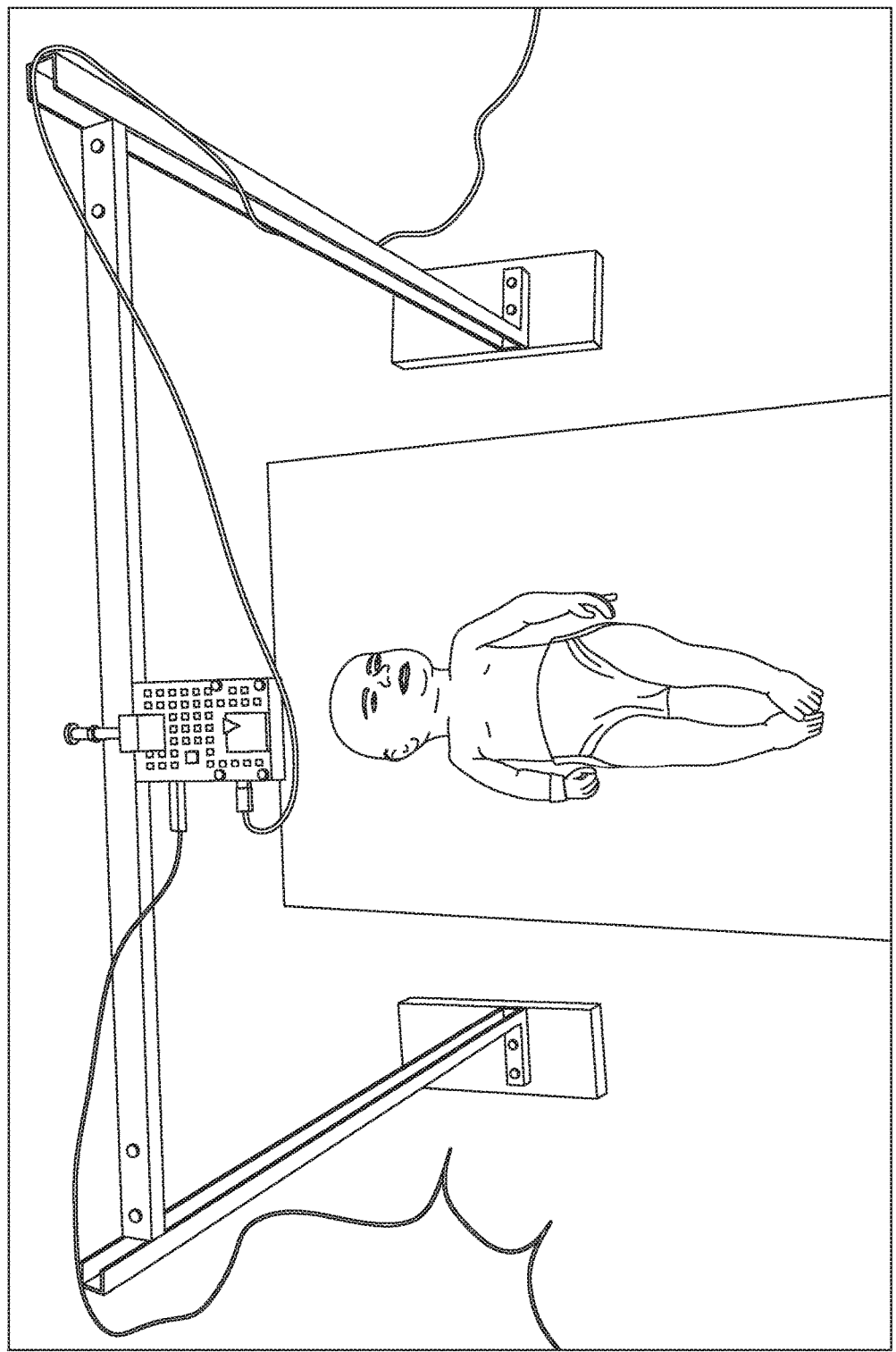
FIG. 6 illustrates an example time-of-flight system to capture a single 3D image of infant subject used to generate a pseudo-skeleton of the subject, according to certain embodiments.

FIG. 6 illustrates an example of a prototype TOF 3D imaging system 1100 to capture a single 3D image of the subject 104. The TOF system 1100 includes a TOF device and a computer. The TOF device emits modulated light and measures the time-of-flight of the reflected light from each point of the surface of a 3D object that is facing the camera. The TOF device may include a TOF component, such as a TI-OPT8241® by Texas Instruments, Inc. In other embodiments, devices that include a camera, such as a digital camera, a tablet, a laptop computer, and the like, can be used to acquire the 3D image. In an embodiment, the included camera is a TOF camera.

The TOF 3D imaging system 1100 acquires a single point-of-view image by emitting infrared light and measuring the delay of the returning light as it is reflected off of the subject to estimate distance. The delay is measured with an array of sensors. In the prototype embodiment illustrated in FIG. 6, a 320×240 array of sensors was used. In other embodiments, the array of sensors comprises more or less sensors.

Figure 7A:
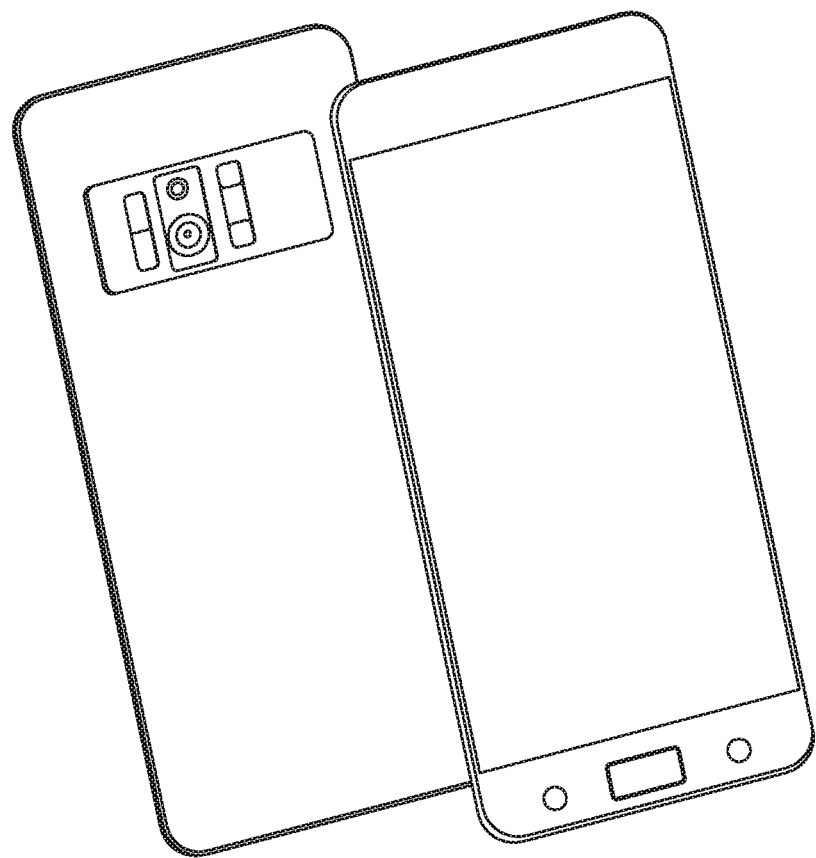
FIGS. 7A and 7B illustrate front and back views of an example of a commercially available TOF camera system used to capture the 3D image of a subject, according to certain embodiments.
Figure 7B:
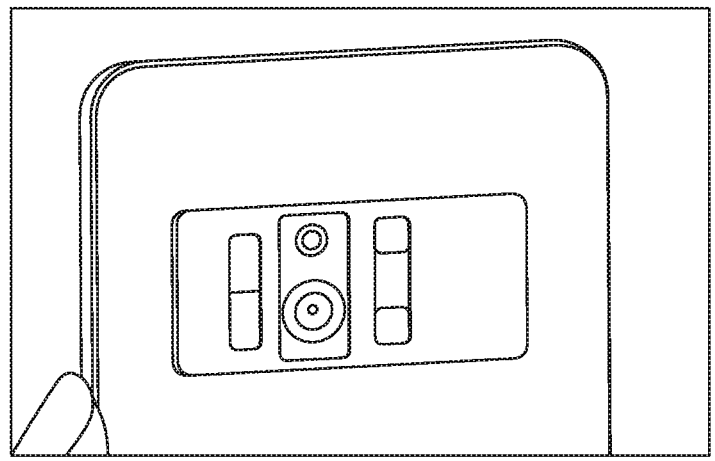

The time-of-flight device can be implemented on a cell phone, such as the ZenFone AR® by ASUS, but could be implemented on other wireless devices, such as laptop computers, digital cameras, and the like. This will provide an easy and convenient way to measure length of infants from frequent, daily photographs provided by infant caregivers in the home setting. Thus, the time-of-flight method offers a way to obtain an estimate of length of an infant from a single 3D image acquired without trained personnel, and using easily available equipment. FIGS. 7A and 7B illustrates the front and back views, respectively, of a commercially available mobile device, the ZenFone AR® by ASUS, which includes a TOF camera.

In other embodiments, the 3D digital image may be obtained from synchronized (i.e., phased) multi-camera TOF systems. To mitigate interference between the images acquired by each TOF camera in the multi-camera TOF system, each TOF camera is paired with a light source, and each light source is operated at a different frequency. In a further embodiment, the 3D digital image may be obtained from a single TOF camera receiving light reflected from the photographed object that is illuminated by multiple light sources, each light source operating at a different frequency.

In addition to TOF, there are other systems and methods to acquire a 3D digital image of the subject that can be processed as described above to determine the change in length over time of the distance on a virtual skeleton between selected natural landmarks.

Figure 8:
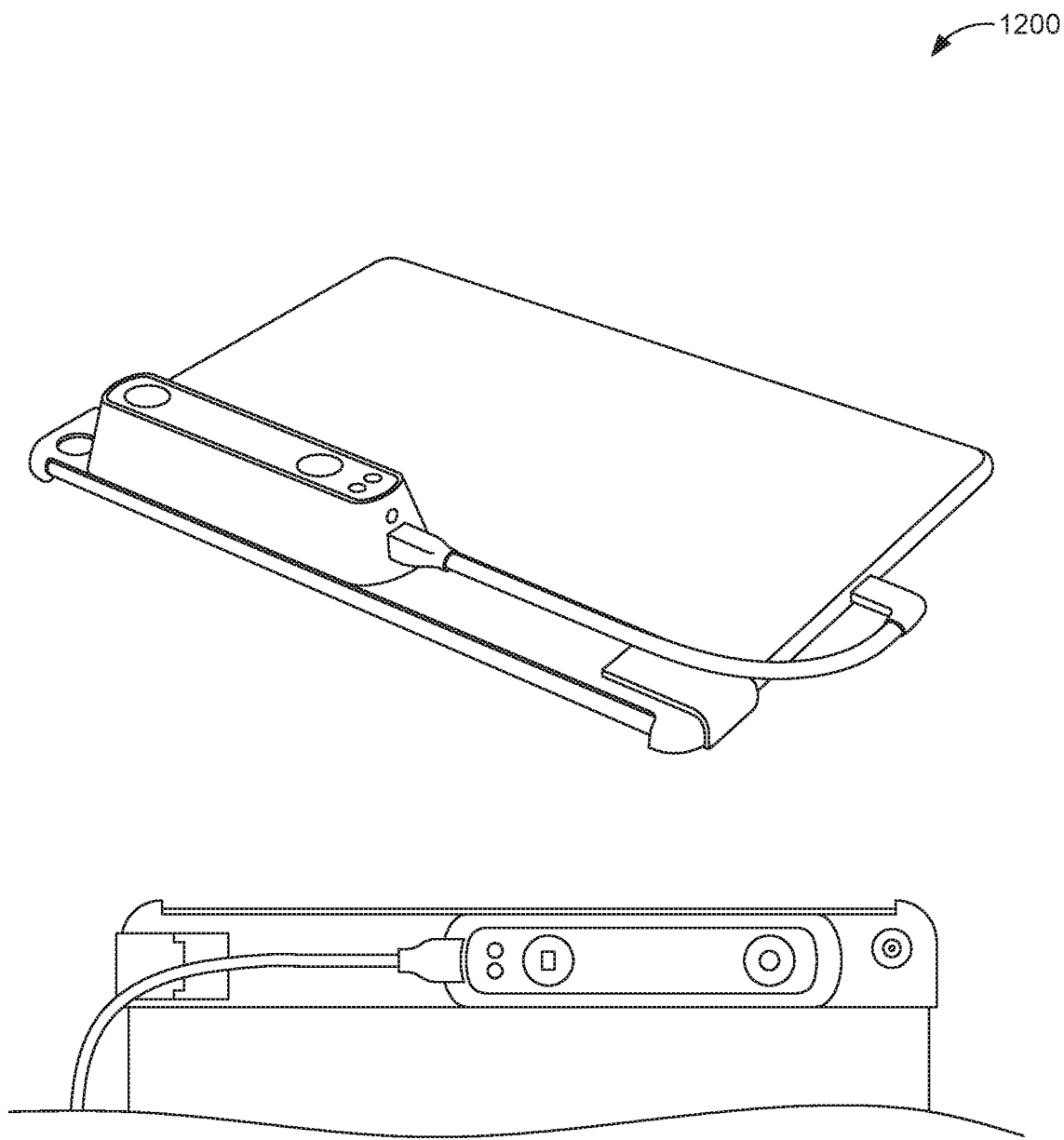
FIG. 8 illustrates front and back views of an example of a stereo camera and structured light system used to capture 3D images of the subject, according to certain embodiments.

FIG. 8 illustrates an example embodiment of a structured light system 1200 used to capture the 3D digital image of the subject 104. A structured-light 3D imaging system includes a scanning device for measuring the three-dimensional shape of an object using projected light patterns and a dual camera system. Projecting a narrow band of light onto a three-dimensionally shaped surface produces a line of illumination that appears distorted from other perspectives than that of the projector, and can be used for a geometric reconstruction of the surface shape.

The structured light system 1200 may comprise a structured-light device, such as Structure Sensor®, attached to an iPhone®. The structured-light 3D imaging system acquires multiple point-of-view images by moving the structured-light device around the subject and, using an image aggregating processor such as the processor in the iPhone® or a computer, dynamically aggregates point-clouds, such as an array of pixels acquired by the structured-light device, to form a 3D digital image of the subject.

In another embodiment, the mat 102 can comprise a clear material, such as a clear acrylic, Plexiglas®, and the like, and images from cameras located below the clear mat can be used to provide information on the back of the subject. This information from the bottom-view can be used to increase accuracy of the position of points on the surface of the subject and improve estimates of length based on the natural landmarks on the front of the subject in the 3D digital image from just the top-view.

Other 3D imaging systems and methods that could be used to acquire 3D digital images are, for example, but not limited to, applying principles of photogrammetry to a standard cell phone camera, other devices using a stereo camera (e.g. commercially available on the Leap®, Lucid®, Blackbird® devices, and the like), and some cell phones with 3D cameras (e.g., ZenFone AR).

These systems provide 3D digital images that can be processed as described above.

Other Embodiments

In an embodiment, a device is embedded in an attachment to an infantometer or scales for weighing an infant, both of which are typically found in medical facilities. The device may comprise a time-of-flight 3D imaging system (such as the PMD CamBoard® system), a structured-light 3D imaging system, a stereo camera system, or the like on an elongated structure, such as a stick ("pixastick"). A photo would be taken before the infant is placed on the infantometer, and then again after placement of the infant, but without alignment of the head or positioning of the legs. The images could be processed using the methods described herein to locate landmarks and to measure the distance between them to provide an indication of the infant's growth.

Weight information from the scale can be used with the estimate of volume from the processed image to provide an indication of the density of the infant. Along with length, weight can be used to provide an estimate of body mass index (BMI), which is used and understood in auxology even though it has technical weaknesses. In an embodiment, the density of the infant is also good indicator of infant growth and overall health.

In another embodiment, a pressure sensitive mat can be used to provide information on the position of critical points (i.e., the back of the head, heel of the foot, etc.) from the back of the infant. The pressure sensitive mat can provide weight information. Sometimes, a bulky diaper can obscure the natural landmarks. The use of a pressure sensitive mat can provide additional information as to the location of the head, hips, and other natural landmarks, based on the pressure measurements when the infant is placed on the pressure sensitive mat. This can overcome any challenges presented by diapers and other clothing.

In another embodiment, a 3D imaging device, such as the time-of-flight imaging device or the like, is placed on an infantometer. With the algorithm supplied in FIG. 1. The device could be mounted on a stand so it is placed over the infant. Either continuously or manually, the 3D imaging device would take images of the empty infantometer and the infantometer with the infant in it, and transmits the images to a storage and processing device, such as a cell phone, computer, or the like, for storage and processing of the series of images.

In another embodiment, multiple time-of-flight devices or cameras can be incorporated in an arrangement at the ends of the infantometer, as well as above the infant. These could be used to obtain better resolution of the head and the feet, which could be added to the length of body parts that are identified from the main image taken from above the infant.

In an embodiment, a two-camera approach to obtain a stereo image is expanded taking multiple images from different perspectives. The cameras can be mounted on the elongated structure ("pixastick") attached to an infantometer. A commercial program, such as Photomodeler™, AutoDesk™, 123D™, or the like, can generate 3D digital images from multiple photos. Once the 3D digital image is acquired, it can be processed as described herein to provide the indication of infant growth.

In another embodiment, a commercially available box designed to provide a safe sleeping place for an infant to prevent or reduce sudden death while sleeping, such as the BabyBox™ and the like can have a device/camera embedded in the four corners or elsewhere in known locations, or the "pixastick" be placed on top, and the multiple images snapped automatically or manually to provide information to generate a 3D digital images. Once the 3D digital image is acquired, it can be processed as described herein to provide the indication of infant growth.

In a further embodiment, 3D images of a fetus generated by ultrasound during pregnancy can be processed as described herein, (filtered, transformed, and landmarks identified) and used to provide the indication of growth of the fetus during pregnancy.

Terminology

Depending on the embodiment, certain acts, events, or functions of any of the algorithms described herein can be performed in a different sequence, can be added, merged, or left out altogether (e.g., not all described acts or events are necessary for the practice of the algorithm). Moreover, in certain embodiments, acts or events can be performed concurrently, e.g., through multi-threaded processing, interrupt processing, or multiple processors or processor cores or on other parallel architectures, rather than sequentially.

All of the processes and steps described above as being implemented by the identification and marketing service may be performed and fully automated by a computer system. The computer system may include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various identification and marketing service functions disclosed herein may be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips and/or magnetic disks, into a different state.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially.

Systems and modules described herein may comprise software, firmware, hardware, or any combinations of software, firmware, or hardware suitable for the purposes described herein. Software and other modules may reside on servers, workstations, personal computers, computerized tablets, PDAs, and other devices suitable for the purposes described herein. Software and other modules may be accessible via local memory, via a network, via a browser, or via other means suitable for the purposes described herein. Data structures described herein may comprise computer files, variables, programming arrays, programming structures, or any electronic information storage schemes or methods, or any combinations thereof, suitable for the purposes described herein. User interface elements described herein may comprise elements from graphical user interfaces, command line interfaces, and other suitable interfaces.

Further, the processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems. Likewise, the data repositories shown can represent physical and/or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Embodiments are also described above with reference to flow chart illustrations and/or block diagrams of methods, apparatus (systems) and computer program products. Each block of the flow chart illustrations and/or block diagrams, and combinations of blocks in the flow chart illustrations and/or block diagrams, may be implemented by computer program instructions. Such instructions may be provided to a processor of a general purpose computer, special purpose computer, or other programmable data processing apparatus to produce a machine, such that the instructions, which execute via the processor of the computer or other programmable data processing apparatus, create means for implementing the acts specified in the flow chart and/or block diagram block or blocks.

These computer program instructions may also be stored in a computer-readable memory that can direct a computer or other programmable data processing apparatus to operate in a particular manner, such that the instructions stored in the computer-readable memory produce an article of manufacture including instruction means which implement the acts specified in the flow chart and/or block diagram block or blocks. The computer program instructions may also be loaded onto a computer or other programmable data processing apparatus to cause a series of operations to be performed on the computer or other programmable apparatus to produce a computer implemented process such that the instructions which execute on the computer or other programmable apparatus provide steps for implementing the acts specified in the flow chart and/or block diagram block or blocks.

While certain embodiments have been described, these embodiments have been presented by way of example only, and are not intended to limit the scope of the disclosure. Indeed, the novel methods and systems described herein may be embodied in a variety of other forms; furthermore, various omissions, substitutions and changes in the form of the described methods and systems may be made without departing from the spirit of the disclosure.

What is claimed is:

1. A computer-implemented method to estimate length of a subject from a three-dimensional image, the computer-implemented method comprising:
    acquiring a three-dimensional image of a subject;
    processing the three-dimensional image of the subject to generate a digital representation of the subject; and
    processing the digital representation of the subject to determine at least a partial length of the subject, wherein the subject is an infant, child, adolescent, or adult.

2. The computer-implemented method of claim 1 wherein said processing the digital representation of the subject to determine at least the partial length of the subject comprises:
    processing the digital representation of the subject to generate a virtual skeleton of the subject; and
    measuring distance along at least a portion of the virtual skeleton to provide an estimate of at least partial length of the subject.

3. The computer-implemented method of claim 2 wherein said processing the digital representation of the subject to generate the virtual skeleton of the subject comprises:
    locating a plurality of peaks and troughs in a point cloud representation of the subject;
    locating a natural landmark associated with human anatomy in each of ones of at least a portion of the plurality of peaks and troughs;
    fitting spheres to model the located natural landmarks; and
    locating centers of spheres to form the virtual skeleton.

4. The computer-implemented method of claim 3 wherein said measuring distance along at least the portion of the virtual skeleton comprises measuring distance between at least two sphere centers along the virtual skeleton to provide the estimate of at least partial length of the subject.

5. The computer-implemented method of claim 3 wherein locating the plurality of peaks and troughs comprises determining derivatives in length and width planes of the point cloud representation of the subject.

6. The computer-implemented method of claim 3 wherein said fitting the spheres comprises detecting a set of extrema on surface of the point cloud representation of the subject and sizing the spheres based on the detected set of extrema.

7. The computer-implemented method of claim 1 wherein the digital representation of the subject comprises a point cloud representation of the subject.

8. The computer-implemented method of claim 1 wherein the three-dimensional image is acquired by a time of flight device.

9. The computer-implemented method of claim 1 wherein the three-dimensional image is generated from a plurality of two-dimensional images.

10. The computer-implemented method of claim 1 wherein the three-dimensional image of the subject comprises a three-dimensional image of the subject on a mat that has defined edges and the digital representation of the subject comprises a digital representation of the subject without the mat.

11. A system to estimate length of a subject from a three-dimensional image, the system comprising:
    one or more computing devices associated with a measurement system, wherein the measurement system is configured to:
    acquire a three-dimensional image of a subject;
    process the three-dimensional image of the subject to generate a digital representation of the subject; and
    process the digital representation of the subject to determine at least a partial length of the subject, wherein the subject is an infant, child, adolescent, or adult.

12. The system of claim 11 wherein said processing the digital representation of the subject to determine at least the partial length of the subject comprises:
    processing the digital representation of the subject to generate a virtual skeleton of the subject; and
    measuring distance along at least a portion of the virtual skeleton to provide an estimate of at least partial length of the subject.

13. The system of claim 12 wherein said processing the digital representation of the subject to generate the virtual skeleton of the subject comprises:
    locating a plurality of peaks and troughs in a point cloud representation of the subject;
    locating a natural landmark associated with human anatomy in each of ones of at least a portion of the plurality of peaks and troughs;
    fitting spheres to model the located natural landmarks; and
    locating centers of spheres to form the virtual skeleton.

14. The system of claim 13 wherein said measuring distance along at least the portion of the virtual skeleton comprises measuring distance between at least two sphere centers along the virtual skeleton to provide the estimate of at least partial length of the subject.

15. The system of claim 13 wherein locating the plurality of peaks and troughs comprises determining derivatives in length and width planes of the point cloud representation of the subject.

16. The system of claim 13 wherein said fitting the spheres comprises detecting a set of extrema on surface of the point cloud representation of the subject and sizing the spheres based on the detected set of extrema.

17. The system of claim 11 wherein the digital representation of the subject comprises a point cloud representation of the subject.

18. The system of claim 11 wherein the three-dimensional image is acquired by a time of flight device.

19. The system of claim 11 wherein the three-dimensional image is generated from a plurality of two-dimensional images.

20. The system of claim 11 wherein the three-dimensional image of the subject comprises a three-dimensional image of the subject on a mat that has defined edges and the digital representation of the subject comprises a digital representation of the subject without the mat.

* * * * *